US009713637B2

(12) United States Patent
Cohen et al.

(10) Patent No.: US 9,713,637 B2
(45) Date of Patent: Jul. 25, 2017

(54) BACILLUS ANTHRACIS HTRA-DEFECTIVE-DERIVED VACCINES

(75) Inventors: Ofer Cohen, Moshav Neta'im (IL); Theodor Chitlaru, Rehovot (IL); Avigdor Shafferman, Nes Ziona (IL)

(73) Assignee: State of Israel Prime Minister's Office Israel Institute for Biological Research, Nes Ziona (IL)

( * ) Notice: Subject to any disclaimer, the term of this patent is extended or adjusted under 35 U.S.C. 154(b) by 0 days.

(21) Appl. No.: 14/232,628

(22) PCT Filed: Jul. 18, 2012

(86) PCT No.: PCT/IL2012/050254
§ 371 (c)(1),
(2), (4) Date: Jan. 14, 2014

(87) PCT Pub. No.: WO2013/011509
PCT Pub. Date: Jan. 24, 2013

(65) Prior Publication Data
US 2014/0170188 A1 Jun. 19, 2014

(30) Foreign Application Priority Data

Jul. 21, 2011 (IL) .......................................... 214246

(51) Int. Cl.
*A01N 63/00* (2006.01)
*A61K 39/07* (2006.01)
*C12N 1/20* (2006.01)
*A61K 39/00* (2006.01)

(52) U.S. Cl.
CPC ................. *A61K 39/07* (2013.01); *C12N 1/20* (2013.01); *A61K 2039/522* (2013.01)

(58) Field of Classification Search
CPC ........... A61K 39/00; A61K 39/07; C12N 1/21
See application file for complete search history.

(56) References Cited

U.S. PATENT DOCUMENTS

| | | | | |
|---|---|---|---|---|
| 5,002,765 | A * | 3/1991 | Herrnstadt et al. | 424/520 |
| 6,994,997 | B1 * | 2/2006 | Poquet et al. | 435/71.1 |
| 7,850,970 | B2 * | 12/2010 | Shapiro | A61K 31/519 424/168.1 |
| 8,591,899 | B2 * | 11/2013 | Shafferman | C07K 14/32 424/139.1 |
| 8,633,305 | B2 * | 1/2014 | Shapiro | 435/320.1 |
| 2005/0103712 | A1 * | 5/2005 | Voyce | 210/645 |
| 2008/0050774 | A1 * | 2/2008 | Berka et al. | 435/69.1 |
| 2009/0209007 | A1 * | 8/2009 | Meima et al. | 435/91.1 |
| 2010/0291246 | A1 * | 11/2010 | Brady | 424/729 |
| 2014/0314716 | A1 * | 10/2014 | Pomerantsev | C12P 21/02 424/93.2 |

FOREIGN PATENT DOCUMENTS

| | | | | |
|---|---|---|---|---|
| WO | 2005/092372 | * | 10/2005 | ............. A61K 39/07 |
| WO | 2009/022162 | * | 2/2009 | ............. C12N 15/75 |
| WO | 2010/109451 | * | 9/2010 | ............. G01N 33/50 |
| WO | 2013/019946 | * | 2/2013 | ............. C12N 1/00 |

OTHER PUBLICATIONS

Aronson, Arthur I et al, Journal of Bacteriology, vol. 187(9), May 2005, pp. 3133-3138, Plasmid encoded Regulator of Extrcellular Protease in Bacillus anthracis.*
Sela-Abramovich, S et al, Applied and Environmental Microbiology, vol. 75(19), Oct. 2009, pp. 6157-6167, Novel and Unique Diagnostic Biomarkers for Bacillus anthracis Infection.*
Zwick, ME et al, Genome Research, vol. 22, pp. 1512-1524, Genomic characterization of the Bacillus cereus sensu lato species: Backdrop to the evolution of Bacillus anthracis.*
Ariel, N et al, Infection and Immunity, Dec. 2002, vol. 70(12), pp. 6817-6827, Search for Potential Vaccine Candidate Open Reading Frames in the Bacillus anthracis Virulence Plasmid pXO1: In Silico and In Vitro Screening.*
Stauff, DL et al, Molecular Microbiology, 2009, vol. 72(3), pp. 763-778, Bacillus anthracis HssRS signalling to HrtAB regulates haem resistance during infection.*
Tjalsma, H et al, Microbiology and Molecular Biology Reviews, Jun. 2004, vol. 68(2), pp. 207-233, Proteomics of Protein secretion by Bacillus subtilis: Separatin gthe "Secrets" of the Secretome.*
Sela-Abramovich, S et al, Applied and Environmental Microbiology, Oct. 2009, vol. 75(19), pp. 6157-6167, Novel and Unique Diagnostic Biomarkers for Bacillus anthracis Infection.*
Chitlaru, T et al, The Challenge of Highly Pathogenic Microorganisms:Mechanisms of Virulence, edited by Avigdor Shafferman year 2010, pp. 11-22, Chapter 2, Proteomic Studies of Bacillus anthracis Reveal In Virtro C)2 modulation and Expression During Infection of Extracellular Proteases, Springer Science and Business Media.*
Chitlaru, T et al, online publication date Jan. 1, 2011, Immunological Reviews, vol. 239,(1), pp. 221-236, Progress and novel strategies in vaccine development and treatment of anthrax.*
Chitlaru, Theodor et al, Molecular Microbiology, 2011, vol. 81(6), pp. 1542-1559, HtrA is a maor virulence determinant of Bacillus anthracis, first published online Aug. 23, 2011.*
Chitlaru, Theodor et al, Journal of Bacteriology, May 2006, vol. 188(10) pp. 3551-3571, Differential Proteomic Analysis of the Bacillus anthracis Secretome: Distinct Plasmid and Chromosome $CO_2$-Dependent Cross Talk Mechanisms Modulate Extracellular Proteolytic Activities.*
Shafferman et al, The Challenge of Highly Pathogenic Microorganisms, Springer , 2010, pp. 38 pages, including pp. 11-22, Chitlaru et al, Proteomic Studies of Bacillus anthracis Reveal In Vitro Co2-Modulation and Expression During Infection of Extracelluar Proteases.*

(Continued)

*Primary Examiner* — Albert Navarro
*Assistant Examiner* — Mark Navarro
(74) *Attorney, Agent, or Firm* — Roach Brown McCarthy & Gruber, P.C.; Kevin D. McCarthy

(57) ABSTRACT

The invention provides an isolated *Bacillus cereus* sensu lato strain, selected from *Bacillus anthracis, Bacillus cereus* and *Bacillus thuringiensis*, in which the htrA gene or any part thereof is silenced, and vaccines comprising the same.

4 Claims, 13 Drawing Sheets

(56) References Cited

OTHER PUBLICATIONS

Chitlaru, Theodor et al, Immunological Reviews, Progress and novel strategies in vaccine Development and treatment of Anthrax, Jan. 2011, pp. 221-236.*
Chitlaru et al, Future Microbiology, 2009, vol. 4(8), pp. 983-998.*
Pomerantseva etal, abstract, Poster Session Monday Jun. 15, 2011, 5th International Conference on Gram Positive Microorganisms, abstract p. 21.*

* cited by examiner

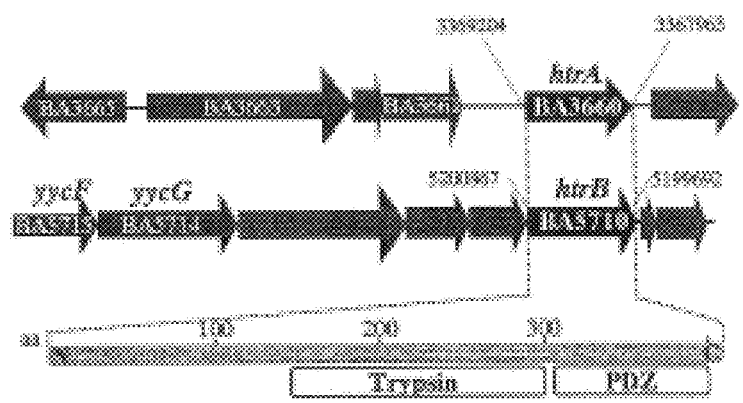
FIG. 1A
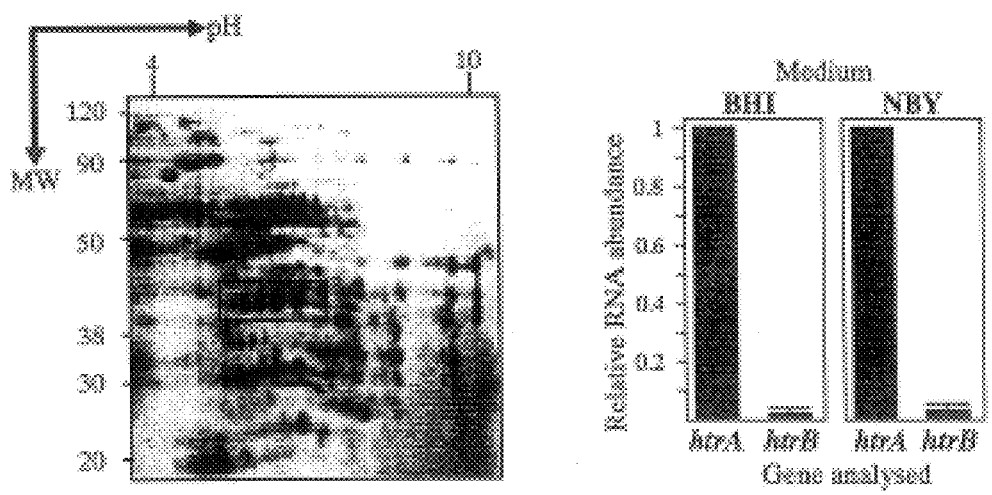
FIG. 1B
FIG. 1C

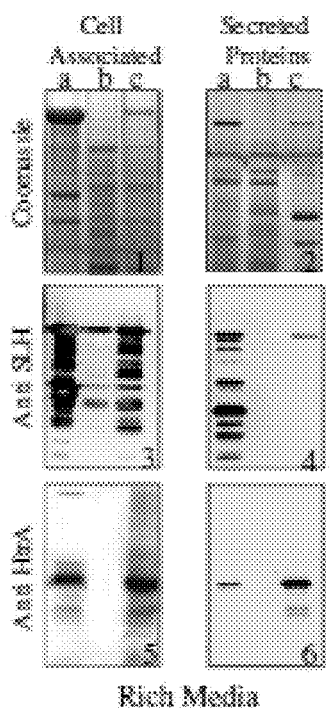
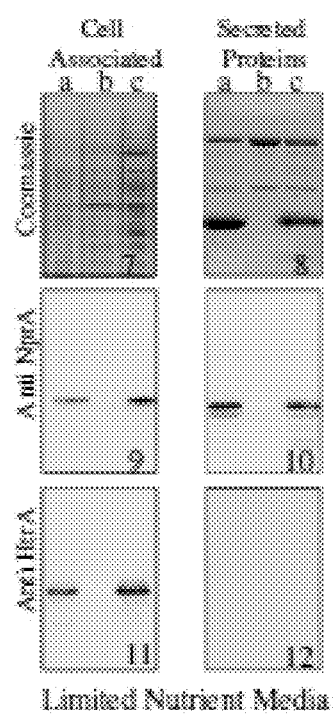
FIG. 3A  FIG. 3B
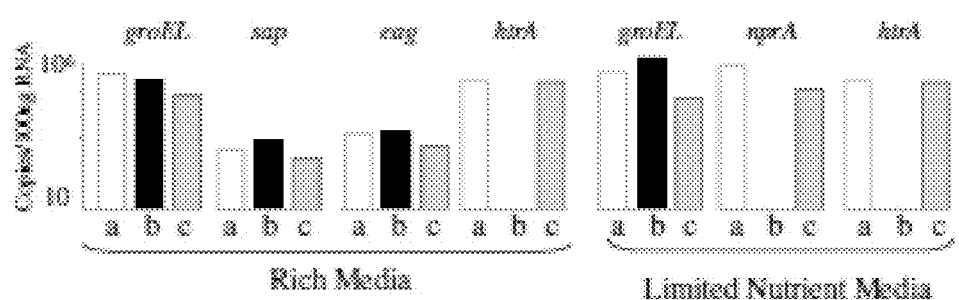
FIG. 3C

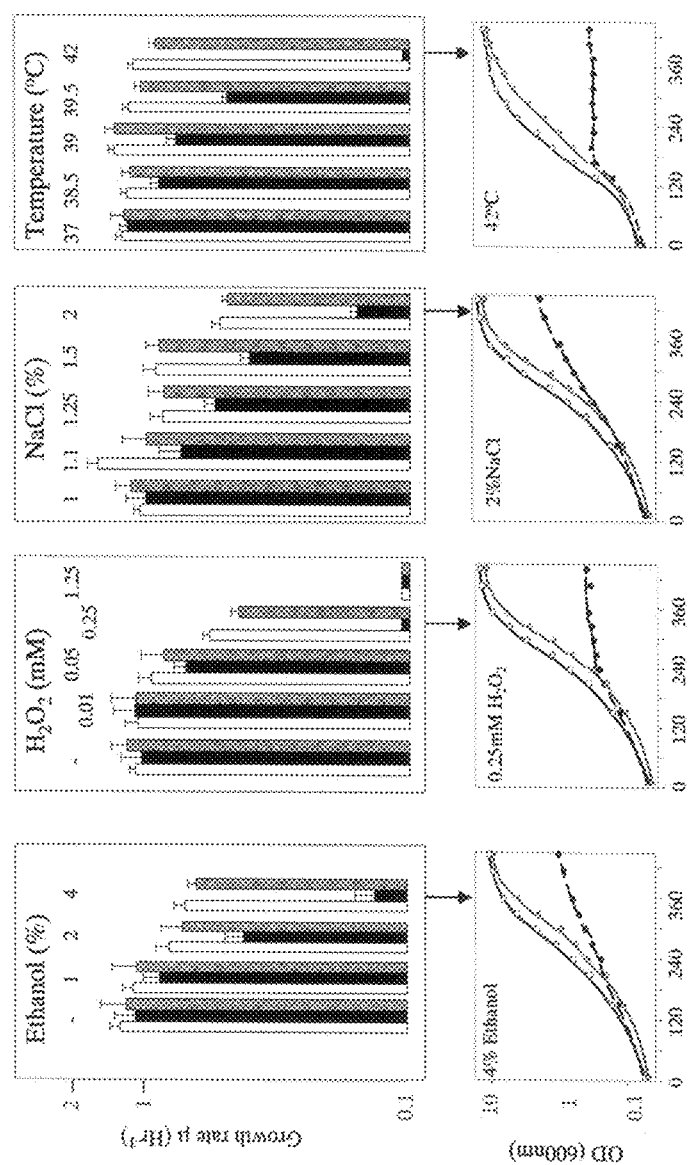

BACILLUS ANTHRACIS HTRA-DEFECTIVE-DERIVED VACCINES

REFERENCE TO CO-PENDING APPLICATIONS

Priority is claimed as a 371 of international application number PCT/IL2012/050254, filed on Jul. 18, 2012; which claims priority to Israeli patent application serial number 214246, filed on Jul. 21, 2011.

FIELD OF THE INVENTION

The present invention relates to infectious diseases. In particular, the present invention relates to vaccine compositions for the prophylaxis of *Bacillus cereus* sensu lato strain, such as *Bacillus anthracis, Bacillus cereus* and *Bacillus thuringiensis*. In one particular aspect the invention relates to the prophylaxis of anthrax.

BACKGROUND OF THE INVENTION

The gram-positive spore-forming obligate-pathogen *Bacillus anthracis* (also referred to as *B. anthracis*) represents the etiological agent of anthrax, a currently rare disease in humans, yet potentially associated with intentional bioterror use. In the most severe respiratory form, *B. anthracis* infection is initiated by inhalation of spores which germinate into fast dividing vegetative cells that secrete toxins and virulence factors during growth in the host, resulting in massive bacteremia and consequently generalized systemic failure and death.

The lethality of anthrax has been attributed to two main aspects of *B. anthracis* pathogenesis: the activity of the bacterial exotoxins and the remarkable proliferous nature of the bacteria in the host. *B. anthracis* secretes two exotoxins, Lethal Toxin (LT) and Edema Toxin (ET) composed of binary combinations of the three proteins Protective Antigen (PA), Lethal Factor (LF) and Edema Factor (EF). PA, the common subunit of both toxins, is not harmful by itself, yet it plays the essential role of binding to a receptor on the surface of host target cells and mediating the intracellular translocation of the lethal subunits of the toxin complex—LF (a zinc protease which together with PA forms the exotoxin LT) and EF (an adenylate cyclase which together with PA constitutes the exotoxin ET). PA elicits a protective immune response and therefore its administration represents the basis for all preventive anthrax countermeasures (Chitlaru et al., 2011) both for pre and post-exposure prophylaxis. The three components of the toxin, are encoded by genes located on pXO1, one of the two virulence plasmids naturally harbored by *B. anthracis*. A second well-established virulence factor is represented by a poly D-glutamate anti-phagocytic capsule synthesized by enzymes encoded by genes located on the second native plasmid pXO2. The virulence of *B. anthracis* is governed by regulatory factors which affect the synthesis of the virulence determinants and which coordinate cross-talk circuits linking chromosome and plasmid located genes.

Anthrax is acknowledged as a toxinogenic disease, owing to the lethality of its major toxins. Yet, during infection, *B. anthracis* secretes a large number of proteins, many of which bear biological functions indicative of a role in the onset and progression of the disease.

For all living organisms, quality control of protein synthesis is a vital activity. One central player in the context of protein quality control is represented by the HtrA (High Temperature Requirement A) family of serine proteases, which are structurally and functionally conserved across a wide range of evolutionary distinct phylogenetic classes both in prokaryots and eukaryots. HtrA proteins exhibit the dual biological activities of chaperones and proteases, and as such, bacterial HtrA has a known function in the turnover of damaged or malfolded proteins that may deleteriously accumulate, particularly under stress conditions. The HtrA family of proteins (often referred as Deg or Do serine protease) was originally identified in *E. coli* as essential for the response to heat shock, and subsequently shown to consist of the three chaperons DegP, DegQ and DegS, active in the correct folding and/or in the proteolytic processing and maturation of some proteins, as well as in the degradation of abnormal exported polypeptides. HtrA proteins, exhibit a characteristic structure, composed of an N-terminal trypsin-like serine protease domain and at least one C-terminal PDZ domain which recognizes substrates and activates the protease function. In *E. coli* and *B. subtillis*, the HtrA family of proteases are important for the survival of the bacteria under different stress regimens. In addition, in Gram positive bacteria, the HtrA chaperones/proteases are closely associated with the SecA membrane-translocation machinery. For example, in *Streptococcus piogenes*, HtrA is localized at the ExportA membranal complex dedicated to the biogenesis of secreted proteins. In some cases, HtrA was invoked as being directly involved in the proteolytic processing or secretion of specific virulence-associated proteins such as SpeB and Hemolysin in *Streptococcus pyogenes*, Pertussis toxin S1 and possibly Adhesin P1 of *Streptococcus mutans*. Furthermore, attenuated *Salmonella enterica* mutated in the htrA gene are effective live vaccines as well as possible vectors for delivery of recombinant heterologous antigens, compatible with human use.

The search for bacterial proteins fulfilling functions which sustain the outstanding ability of *B. anthracis* to expand in the host represented the objective of extensive genomic-proteomic-serologic screens of *B. anthracis* surface and secreted proteomes (reviewed in Chitlaru et al., 2009, and in Shaferman et al., 2010). Based on these studies, a list of immunogenic proteins could be assembled, many of which representing potential novel *B. anthracis* virulence factors (Chitlaru et al., 2007; Gat et al. 2006) for subsequent studies addressing their ability to serve as the basis for future improved vaccines, therapeutic intervention and diagnostics. HtrA was distinguished in these studies (i) by its assignment to a regulon which comprises secreted proteins exhibiting a pattern of expression similar to that of the toxin (elevated expression in the presence of $CO_2$), (ii) by its high immunogenicity which indicates in-vivo expression in the host, and (iii) by the observation that significant amounts of HtrA can be detected in the circulation of infected animals relatively early in infection (WO2010/109451; Sela Abramovich et al., 2009). By examining the phenotype associated with disruption of the htrA gene, the present invention provides evidence that HtrA is directly or indirectly involved in the export of some bacterial secreted factors (other than the bacterial toxin), is required for the resistance of *B. anthracis* to stress conditions, it is unexpectedly essential for manifestation of *B. anthracis* virulence, and most importantly *B. anthracis* strains in which htrA gene was disrupted represent efficacious and safe immunization means for providing protection against *B. anthracis* infection.

It is an object of the present invention to provide an isolated *Bacillus anthracis (B. anthracis)* strain in which the htrA gene of said *B. anthracis* is silenced. Thus, encompassed by the invention is such a strain in which the htrA gene is mutated by the removal of said gene.

It is another object of the invention to provide an isolated *Bacillus anthracis* (*B. anthracis*) strain in which the htrA gene of said *B. anthracis* is silenced, which can be used for the preparation of a vaccine.

It is yet another object of the invention to provide an isolated *B. anthracis* strain in which the htrA gene of said *B. anthracis* is disrupted, which can be used as a platform for expression and protective immunization with homologous and heterologous bacterial antigens

SUMMARY OF THE INVENTION

In one aspect the invention relates to an isolated *Bacillus cereus* sensu lato strain, selected from *Bacillus anthracis*, *Bacillus cereus* and *Bacillus thuringiensis*, in which the htrA gene or any part thereof is silenced. One strain of particular interest is the *Bacillus anthracis* (*B. anthracis*).

Accordingly, in one aspect the invention relates to an isolated *B. anthracis* strain in which the htrA gene or any part thereof is mutated by removal of the nucleotide sequence set forth in SEQ ID NO: 27 from the genome of said *B. anthracis* strain. Thus in one aspect the invention relates to a *B. anthracis* mutant strain having a disrupted, partially disrupted or mutated htrA gene.

In another aspect the invention relates to a vaccine comprising the isolated strain of *Bacillus cereus* sensu lato strain. An illustrative example of such vaccine is that which comprises the abovementioned *B. anthracis* mutant strain.

The vaccines according to the invention are useful for the prophylaxis of anthrax infection in a mammalian subject in need thereof.

The invention further encompasses the use of an isolated *B. anthracis* strain, expressing a homologous and/or a heterologous DNA integrated therein, for the preparation of a vaccine.

Similarly, the invention encompasses the use of an isolated *B. anthracis* strain, expressing a homologous and/or a heterologous antigen, for the preparation of a vaccine.

The invention is further directed to an isolated *B. anthracis* strain that is suitable as a backbone for the preparation of a vaccine against a heterologous infectious pathogen.

In another aspect the invention is directed to an isolated *B. anthracis* or a *B. anthracis* mutant strain, for use in the prophylaxis of anthrax, particularly for use in the preparation of a vaccine for the prophylaxis of anthrax.

All the above and other characteristics and advantages of the invention will be further understood through the following illustrative and non-limitative description of embodiments thereof, with reference to the appended drawings. In the drawings the same numerals are sometimes used to indicate the same elements in different drawings.

BRIEF DESCRIPTION OF THE DRAWINGS

FIG. 1A-1C: The HtrA and HtrB paralogue serine proteases of *B. anthracis*

FIG. 1A: Schematic representation of the *B. anthracis* chromosomal loci and genomic context of BA3660 and BA5710 encoding for the two paralogue serine proteases referred to herein as HtrA and HtrB. Both proteins exhibit the characteristic PDZ and Trypsin domains of the HtrA family of stress proteases/chaperones (called also Deg). The gene BA3660 is monocistronic while BA5710 is located in the yycF/G operon. The chromosomal coordinates of the nucleotides flanking the genes are indicated, according to the *B. anthracis* "Ames-ancestor" genome (in the NCBI repository) which serves as a reference for the *B. anthracis* genomic data.

FIG. 1B: Representative two-dimensional gel electrophoresis (two-DE) analysis of secreted proteins collected from a *B. anthracis* rich-media culture. The protein spots representing HtrA are indicated by a rectangle in the Commassie-blue stained gel. The identity of the protein spots was determined by MALDI-TOF MS analysis. HtrB protein spots were not detected in any of the proteomic surveys of the bacterial secreted or surface associated proteins in none of the various conditions examined.

FIG. 1C: Relative expression of the htrA and htrB genes. RNA was extracted from rich BHI (left panel) or low-nutrient NBY (right panel) cultures, and subjected to Q-RT-PCR with htrA and htrB specific primers, as described in Experimental Procedures. The amount of htrB specific RNA in each of the 3 independent experiments carried out is expressed as a fraction of the htrA RNA level.

FIG. 2A: Disruption of htrA gene in the background of ΔVollum (pXO1⁻, pXO2⁻) results in complete abrogation of HtrA expression. Analysis of cell pellets (upper panels) and secreted proteins (lower panels) collected from BHI cultures of ΔV and ΔVΔhtrA at the indicated time-points representing logarithmic (4 hours), transition (6 hours) and stationary (10 hours) growth phases (see growth curves in B). Left panels: commassie blue stained gels; right panels: Western blots probed with anti HtrA antibodies.

FIG. 2B: Growth curves of parental ΔV (grey dots) and ΔVΔhtrA (black dots) BHI cultures.

FIG. 2C: Temperature dependent growth of the parental ΔV, mutated ΔVΔhtrA and complemented ΔVΔhtrA/HtrA colonies on LB-agar plates at 30° C., 37° C. and 42° C. Bacteria were collected from logarithmically growing cultures (at 37° C.) and decimal dilutions plated by spotting 10 μl on LB-agar plates.

FIG. 2D: Q-RT-PCR analysis using htrA (left panel) and htrB primers (right panel) of RNA extracted from cultures (7 hours in NBY) of the parental ΔV and mutated ΔVΔhtrA strains. Specific cDNA copy numbers are expressed as a fraction of the expression level determined for htrA in the parental ΔV strain. Histograms represent the average of three independent experiments.

FIG. 2E: Two-DE analysis of secreted proteins collected from 8 hours rich media (gels 1 and 2) and low-nutrient media (gels 3 and 4) of the parental ΔV (gels 1 and 3) and mutated ΔVΔhtrA (gels 2 and 4) strains. Only protein spots representing EA1, Sap, HtrA and NprA are framed in the parental ΔV gels, as well as the empty position of these spots in the mutated ΔVΔhtrA strain.

FIGS. 3A-3C: HtrA dependent expression of S-Layer proteins Sap and EA1, and NprA in the background of the ΔV (pXO1⁻, pXO2) strain FIG. 3A: Coomassie-blue staining and Western blot analysis assessing expression of S-layer proteins Sap and EA1 by the parental ΔV (lanes marked a), the mutated ΔVΔhtrA (lanes marked b) and the complemented ΔVΔhtrA/HtrA (lanes marked b) strains, grown in rich FAG media. Panels 1 and 2 represent coommassie blue-stained gels of cell associated and secreted proteins, respectively; 3 and 4 are Western blots of cell associated (3) and secreted proteins (4), probed with anti-SLH domain antibodies, recognizing both Sap and EA1; 5 and 6 are similar blots probed with anti-HtrA antibodies.

FIG. 3B: Coomassie blue and Western blot analyses assessing expression of the secreted protease NprA by the parental ΔV, mutated ΔVΔhtrA and complemented ΔVΔhtrA/HtrA strains, grown in rich NBY media. Designations of electrophoretic lanes are as in A; 7 and 8 represent coomassie blue-stained gels of cell associated and secreted proteins, respectively; 9 and 10 are Western blots of cell associated and secreted proteins, respectively, probed with anti-NprA antibodies; 11 and 12 are similar blots probed with anti-HtrA antibodies.

FIG. 3C: Q-RT-PCR analyses assessing expression of S-layer proteins Sap and EA1 and of the secreted protease NprA by the parental ΔV (white histograms marked a), mutated ΔVΔhtrA (black histograms marked b) and complemented ΔVΔhtrA/HtrA (grey histograms marked c) strains, grown in rich FAG media or NBY limited nutrient medium, as indicated. The genes examined by the various Q-RT-PCR analyses are indicated above the respective histograms. Note that the decrease in the level of the S-layer proteins is not accompanied by diminution of the RNA levels of the sap and eag genes, while the decrease in the level of NprA is accompanied by a complete transcriptional silencing of the nprA gene. Q-RT-PCR of groEL served as a positive control.

FIG. 5A: Left panels: Phase microscope visualization of the capsule on cells of the parental and htrA disrupted-mutant, by Indian-ink staining. The capsule appears as a white halo surrounding the bacilli. Right panels: Western blot analysis of proteins secreted by the indicated strains cultured under toxin and capsule inducing conditions (NBY—$CO_2$), probed with the indicated antibodies against HtrA and toxin components.

FIG. 5B: PA level in the peripheral circulation of individual animals infected with the indicated dozes of VΔhtrA strain. The levels of PA determined in blood samples collected 48 hours post inoculation of guinea pigs with VΔhtrA spores, is depicted as a black dots. The median value of the levels exhibited by animals within same experimental group is depicted as a grey histogram. LOQ (limit of quantification) denotes the limit of PA quantification enabled by the PA specific ELISA.

FIGS. 6A-6D: Phenotypic behavior of the VollumΔhtrA cells, under different stress-inducing conditions.

FIGS. 6A-6D: Growth rates of parental Vollum (white histograms), VΔhtrA (black histograms) and VΔhtrA/HtrA (grey histograms) cultured in BHI supplemented with the indicated final concentrations of Ethanol (A), $H_2O_2$ (B), NaCl (C), or grown at different temperatures (D). Under each panel, the actual growth profiles of the three strains at the indicated concentration of stress inducing compound is depicted (Vollum, white circles; VΔhtrA, black circles; VΔhtrA/HtrA, grey circles). All cultures were tested 3 times in duplicated experimental groups.

Figure 7A:
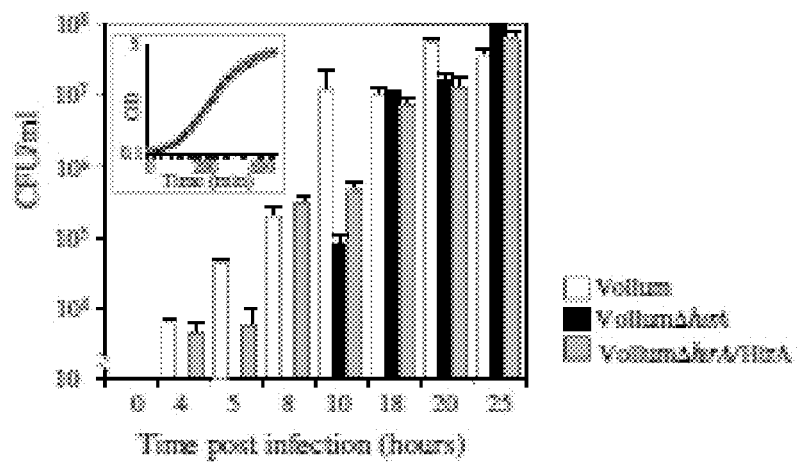
FIGS. 7A-7B: phenotypic behavior of the VollumΔhtrA cells, in the J774.1 macrophage infection assay.
Figure 7B:
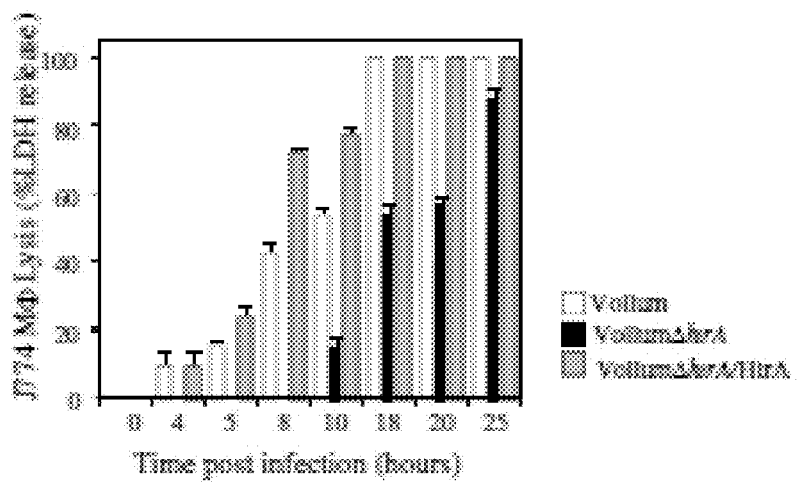

Cells of the J774.1 macrophage line were infected either with wild type Vollum (white bars), VollumΔhtrA (black bars), or with VΔhtrA/HtrA complemented strain spores (grey bars). Samples were withdrawn at the indicated times, and evaluated by (FIG. 7A) the amount of free bacteria released from the cells as measured by viable plate counting and (FIG. 7B) macrophage (MΦ) lysis measured by LDH release to the culture growth medium. 100% lysis was determined by the total LDH activity determined in mock-infected cells released by treatment with 0.2% Tryton×100. The experiment was set up in triplicate experimental groups. The inset in FIG. 7A depicts the growth profiles of the 3 strains in DMEM.

Figure 8A:
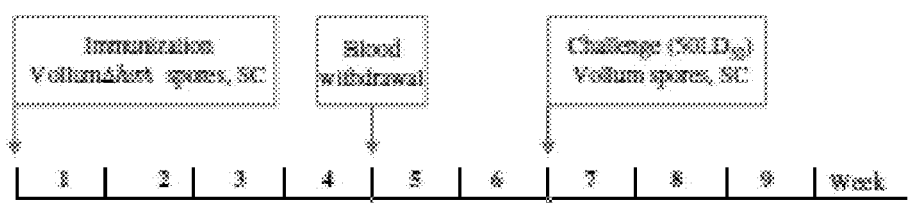
Figure 8B:
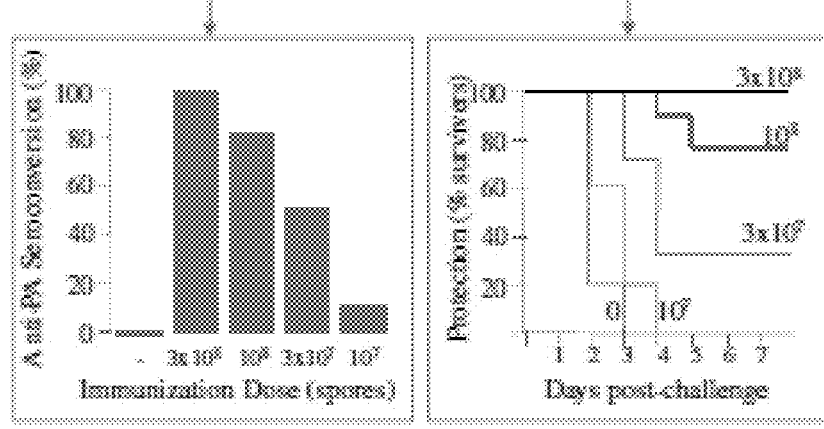

FIGS. 8A-8B: Single administration of sub-lethal doses of attenuated Vollum ΔhtrA spores protect guinea pigs against challenge with fully virulent B. anthracis spores.

FIG. 8A: Schedule (in weeks) of immunization, blood withdrawal and challenge.

FIG. 8B: Guinea pigs (5-10 animals/group) were immunized with doses of Vollum ΔhtrA spores ranging from $10^7$ (0.03 $LD_{50}$) to $3 \times 10^8$ (1 $LD_{50}$). All animals survived immunization except for the 1 LD50 group in which, as expected, a 60% survival of the animals was observed. Left panel: histograms show the percentage of animals which exhibited anti PA-antibodies 4 weeks post immunization. Right panel: survival rate of animals immunized with the indicated dozed of V ΔhtrA, challenged 6 weeks post immunization with 50 $LD_{50}$ of fully virulent Vollum spores.

Figure 9A:
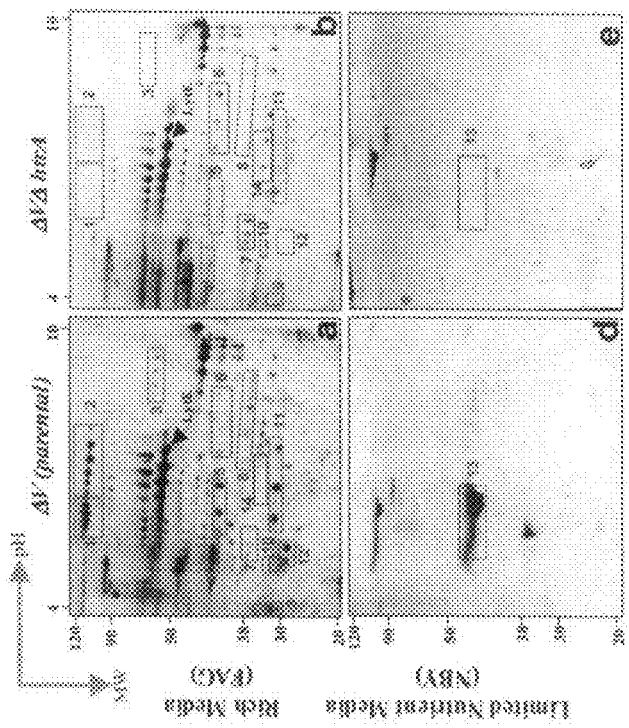
Figure 9B:
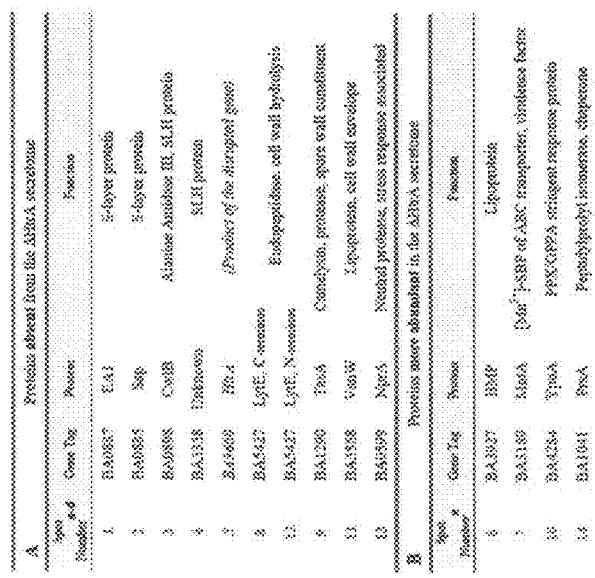

FIGS. 9A-9B: Differential proteomic analysis of the ΔVΔhtrA and the parental ΔV strain secretomes FIG. 9A: Two types of culture supernatants were inspected for the ΔVΔhtrA and the ΔV strains: one from the FAG rich media (panels a, b) and one from the limited nutrient media NBY (panels d, e). Gels were stained with Coomassie blue. Spots representing differentially expressed proteins are numbered. Note the dramatic down modulation of spots 1 and 2 (representing the S-layer proteins EA1 and Sap) and 13 (representing the protease NprA) caused by htrA disruption.

FIG. 9B: Secreted proteins exhibiting alterations in their abundance in the ΔVΔhtrA compared to the parental ΔV strain are tabulated according to their respective spot numbers and divided into two categories: A: proteins absent from the secretome of the ΔhtrA strain; B: proteins which are absent from the secretome of the parental wild type strain.

[a] The disappearance from the secretome of spots 1 (EA1), 2 (Sap), 5 (HtrA itself, marked in italics) and 13 (NprA) is extensively discussed in the hereinbelow.

[b] Spots 3 and 4 represent proteins which contain SLH (S-layer homology) domains. Their absence from the mutated strain may indicate that in addition to Sap and EA1, the abundance of other SLH-containing proteins is affected, as well.

[c] The spots representing the full-size protein LytE are indicated. The abundance of this protein is not altered upon htrA disruption, yet the two isoforms representing N and C terminal domains (spots 8 and 12, respectively) could be detected only in the parental (htrA+) strain secretome. This HtrA dependent appearance of LytE sub-fragments strongly argues in favor of an involvement (direct or indirect) of HtrA in proteolytic processing of at least some bacterial proteins.

[d] TasA and VanW are extracellular proteins whose secretion may depend on HtrA.

[e] Proteins BMP, MntA, YpuA and PrsA, which are more abundant in the htrA mutated strain are all exported polypeptides containing N-terminal signal sequences. BMP, MntA and PrsA are lipoproteins exhibiting the characteristic anchorage cysteine containing N-terminal domain. PrsA is a chaperone with a potential function in the secretion of the toxin. MntA is a demonstrated virulence determinant of *B. anthracis*.

Figure 10:
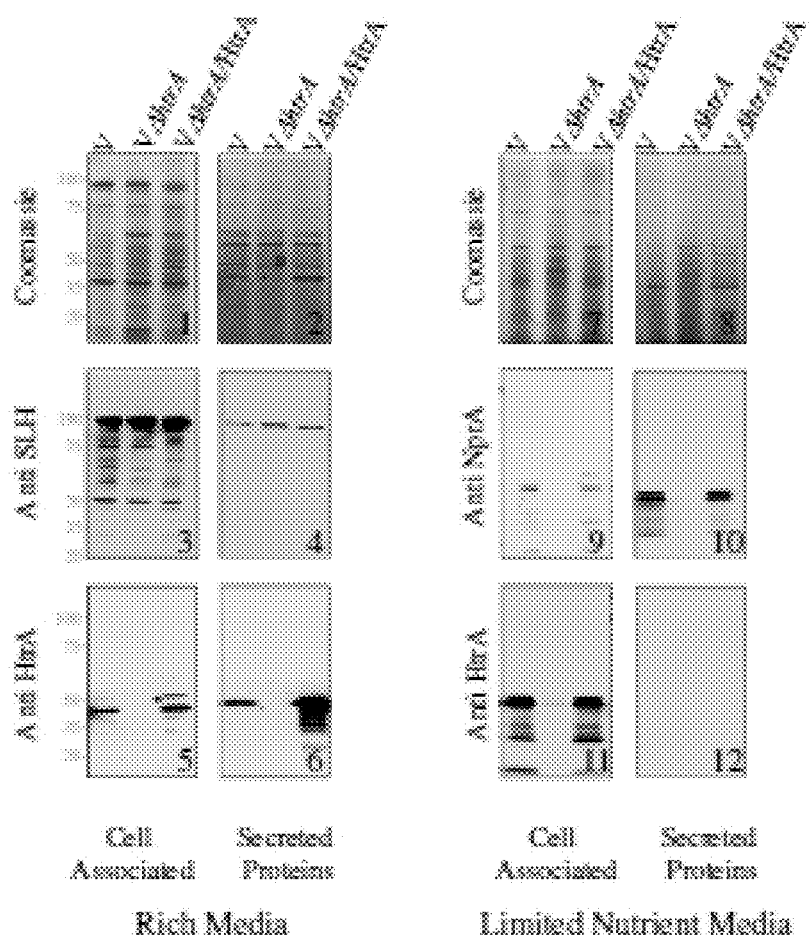

FIG. 10: The VΔhtrA bacteria express unaffected levels of the S-layer proteins Sap and EA1 but do not express the extracellular protease NprA Coomassie blue and Western blot analysis of Vollum, VΔhtrA and VΔhtrA/HtrA cell pellets or secreted proteins collected from BHI rich media (left panels 1, 2, 3, 4, 5, 6) or NBY low nutrient media (right panels 7, 8, 9, 10, 11, 12). Upper panels: Coomassie blue stained gels; middle and lower panels: corresponding Western blots, probed with anti SLH-domain antibodies (panels 3 and 4), anti-NprA antibodies (panels 9 and 10) and anti-HtrA antibodies (panels 5, 6, 11, 12).

Figure 11A:
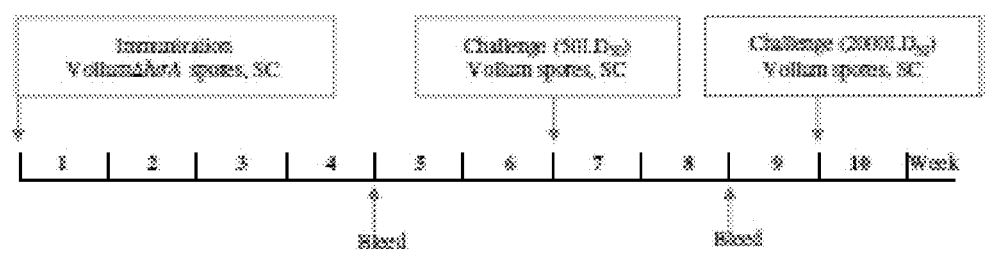
Figure 11B:
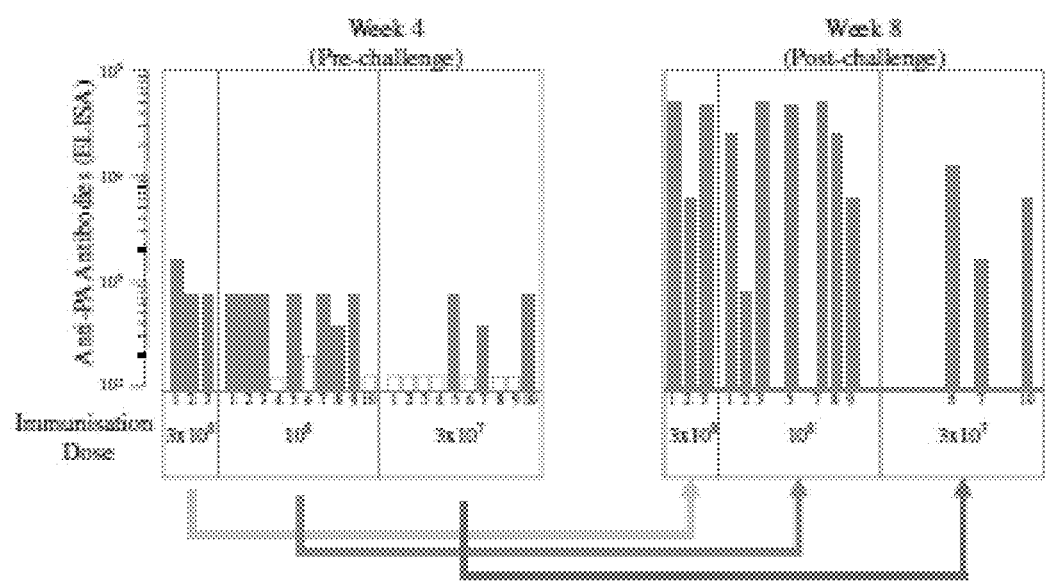

FIGS. 11A-11B: Immunization with VΔhtrA spores elicits a protective immune response in guinea pigs FIG. 11A: Schematic representation of immunization and challenge schedule.

FIG. 11B: Guinea pigs were immunized with the indicated doses of spores (10 animals per group immunized with $3 \times 10^7$ and $10^8$; 5 animals in the group immunized with $3 \times 10^8$ spores). Three out of ten animals immunized with $3 \times 10^8$ spores survived the immunization. Histograms represent the anti PA titers measured in individual animals 4 weeks post-immunization (left panel; individual animals are identified by numbers under their respective histogram). All animals exhibiting anti-PA antibody titers higher than 200 survived a first challenge with 50 $LD_{50}$ fully virulent Vollum spores. Histograms representing the titers of the animals which survived the challenge are shadowed. All animals that did not survive the challenge are absent from the right panel (boost effect) while all animals which survived the first challenge developed high titers of antibodies and survived a second challenge with 2000 $LD_{50}$ virulent Vollum spores.

Figure 12A:
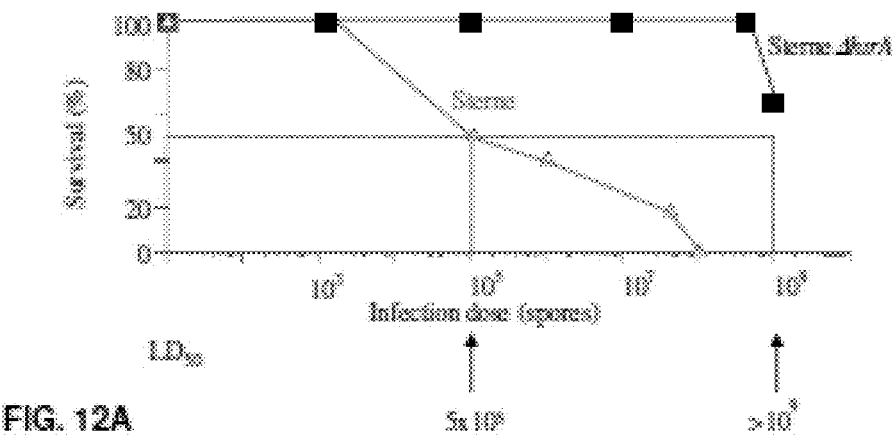
Figure 12B:
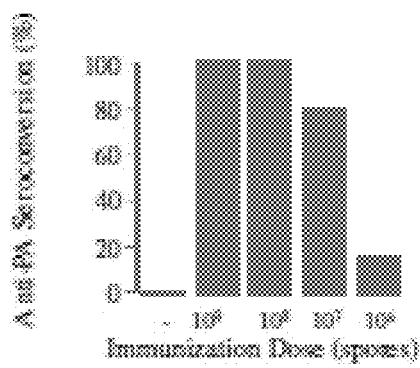
Figure 12C:
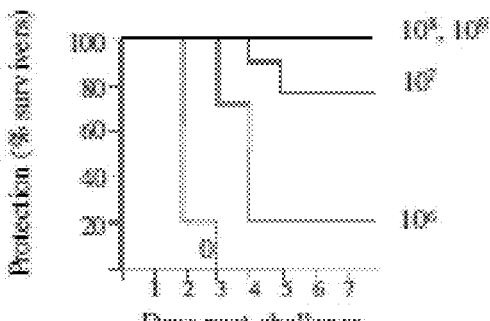

FIGS. 12A-12C: Influence of htrA disruption on the virulence of *B. anthracis* Sterne Strain in the guinea pig model of anthrax.

FIG. 12A: Survival rates of guinea pigs inoculated subcutaneously with spores of the strains Sterne (grey circles and curve) and Sterne ΔhtrA. The LD50 values determined for the parental and mutated strains are indicated. Each experimental group included at least 5 animals. Animals were monitored 3 weeks post inoculation.

FIG. 12B: Single administration of sub-lethal doses of attenuated Sterne ΔhtrA spores elicits a humoral anti-PA response in guinea pigs. Guinea pigs (5-10 animals/group) were immunized with doses of Sterne ΔhtrA spores ranging from $10^7$ (0.01 $LD_{50}$) to $10^9$ (<1 $LD_{50}$). All animals survived immunization except for the $10^9$ group in which, as expected, a 60% survival of the animals was observed (see FIG. 12A). Four weeks post-immunization, blood was withdrawn from all animals for evaluation of anti-PA antibody titers. The data represents the average of two independent immunization experiments using different spore preparations and animal batches. Histograms show the percentage of animals which exhibited anti PA-antibodies.

FIG. 12C: Single administration of sub-lethal doses of attenuated Vollum ΔhtrA spores protect guinea pigs against challenge with fully virulent *B. anthracis* spores. Curves describe survival rates of animals immunized with the indicated doses of SterneΔhtrA, challenged 6 weeks post immunization with 50 LD50 of fully virulent Vollum spores.

FIGS. 13A-13D: Use of *B. Anthracis* attenuated spores for expression of heterologous proteins FIG. 13A: A shuttle vector (Gat et al., 2003) used to express both or either one of the antigens PA and the *Y. pestis*-derived V antigen.

Figures 13A, 13B, 13C, 13D:
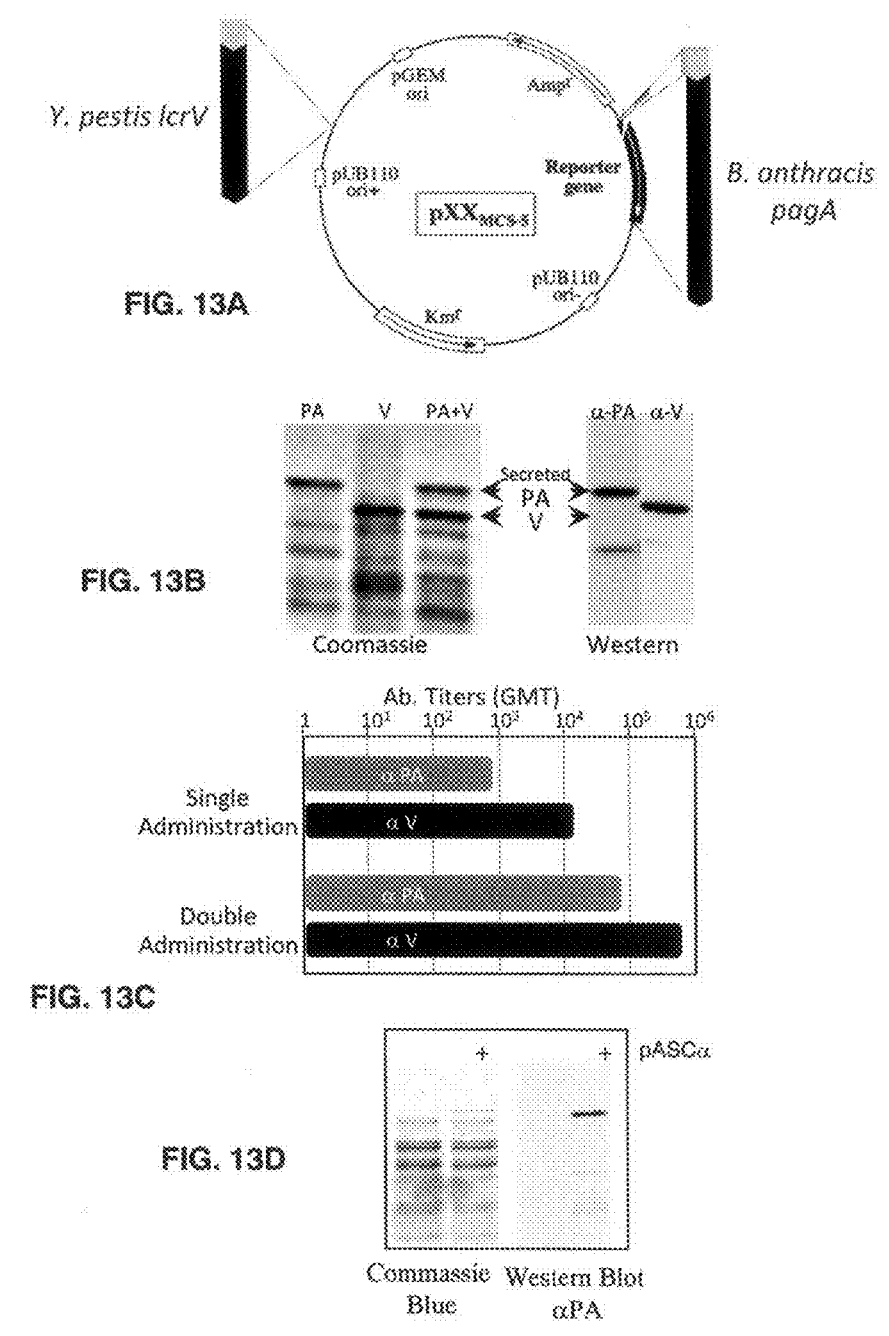

FIG. 13B: Bacteria engineered by transformation with the shuttle vector (in FIG. 13A) express and secrete into the culture media both antigens. The figure depicts Western blot analysis using specific anti-PA and anti V.

FIG. 13C: Mice immunized with a single or double (11 weeks apart) with $10^8$ spores/mouse, exhibit high titers of anti PA and anti-V antibodies. Histograms represent the average titers measured by ELISA 4 weeks post 1st immunization and 2 weeks post 2nd administration. All seroconverted mice were protected against a SC challenge with either fully virulent *B. anthracis* Sterne strain (1000 LD50) or the *Y. pestis* Kim 53 strain (50 LD50).

FIG. 13D: *B. anthracis* bacteria of the ΔVollum strain, disrupted in the unique htrA gene, as described hereinbelow, were transfected with a PA gene-containing shuttle vector (see FIG. 13A), as indicated. Western blot analysis demonstrates that the htrA mutated strain secretes into the culture media significant amounts of recombinant PA. Therefore, this strain is suitable for expression of heterologous antigens in vivo and in vitro.

DETAILED DESCRIPTION OF THE INVENTION

The invention will now be described with reference to specific examples and materials.
The htrA Locus of *Bacillus anthracis*, Philogenetic Similarity with *B. cereus* Group Orthologues, Genomic Organization and htrA Targeted Disruption Phylogenetically, *B. anthracis* belongs to the group of spore-forming soil bacilli known as *Bacillus cereus* sensu lato which also includes *B. cereus, B. mycoides, B. pseudomycoides* and *B. thuringiensis*. Despite the high degree of physiological and morphologic similarity, as well as extensive chromosomal-DNA sequence homology (for example, Rasko et al.), only *B. anthracis* is highly pathogenic, while human infections by *B. cereus* and *B. thuringiensis* are rare and in most of the cases, not life threatening. Members of the *Bacillus cereus* group may be regarded as one strain among which, *B. anthracis* is discerned by the presence of the pXO1 and pXO2 virulence plasmids (encoding 140 and 80 genes, respectively) which confer its unique ability to produce the anthrax-causing toxin. The htrA gene, whose disruption in *B. anthracis* represents the basis of the present invention, is remarkably conserved among all members of the *Bacillus cereus* sensu lato group. For example, HtrA from *B. anthracis* (locus tag BA3660), from *B. thuringiensis* (NCBI locus tags in the Al Hakam strain BALH_324 and in the Kunkukian strain, BR9727_3357), from *B. cereus* (NCBI locus tags in the E33L strain BCZK3307 and in strain G9241 strain BCE_G9241_3552) exhibit complete conservation—100% identity in the amino acid sequence.

Figure 2A:
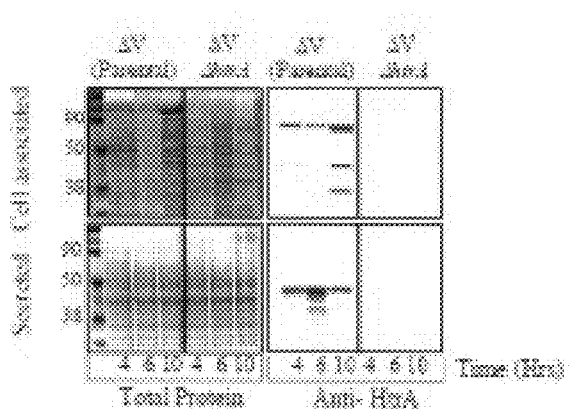
FIGS. 2A-2E: Characterization of *B. Anthracis* ΔVΔhtrA cells.
Figure 2C:
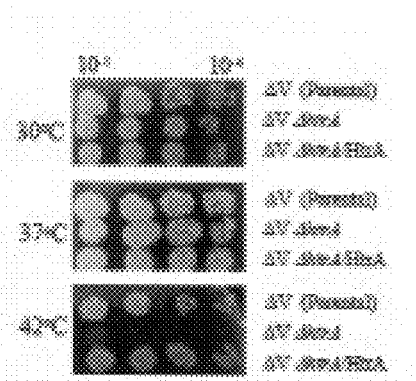
Figure 2B:
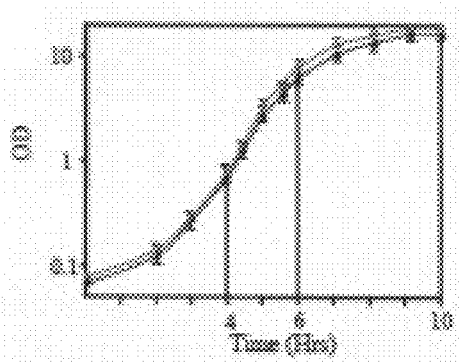
Figure 2D:
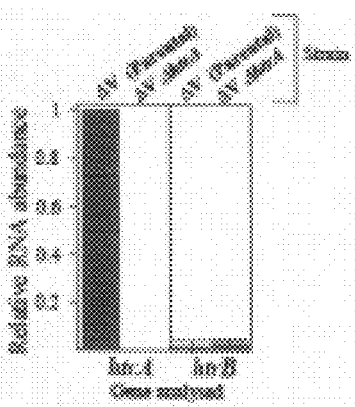
Figure 4:
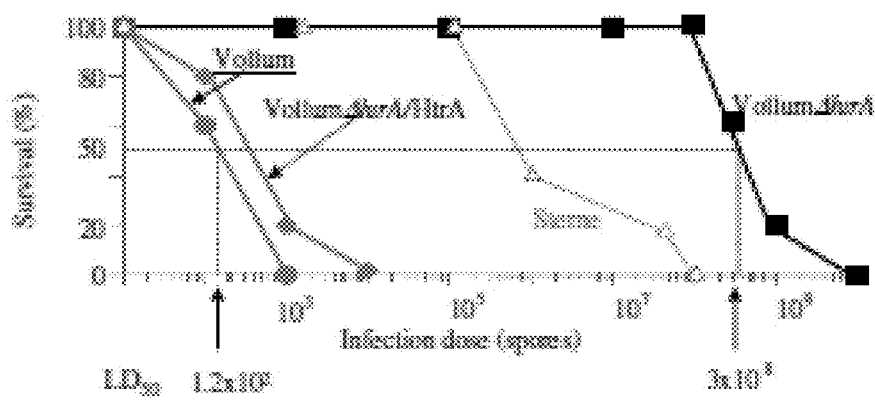
FIG. 4: Influence of htrA disruption on the virulence of B. Anthracis in the guinea pig model of anthrax Survival rates of guinea pigs inoculated sub-cutaneously with spores of the strains Vollum (grey circles and curve), VΔhtrA (black squares and curve), VΔhtrA/HtrA (grey diamonds/dotted curve) and Sterne (pXO1+, pXO2−; open triangles/thin curve). The $LD_{50}$ values determined for the parental and mutated strains are indicated. Each experimental group included at least 5 animals. Animals were monitored 3 weeks post inoculation. The mean time to death (MTD) recorded for succumbed animals was 2-3 days and did not vary in the various groups.
Figure 5A:
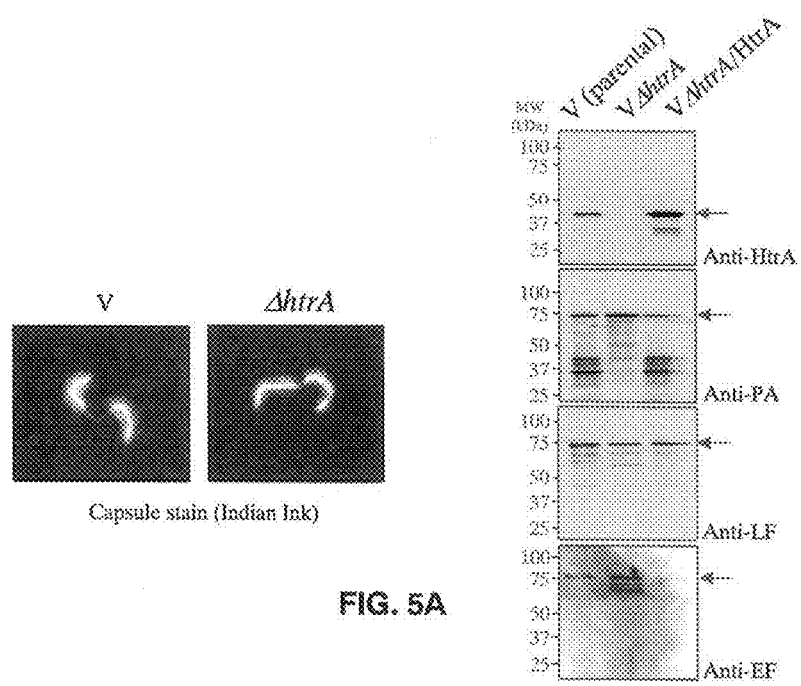
FIGS. 5A-5B: The VΔhtrA strain produces the components of the B. anthracis Toxins PA, LF and EF, as well as the antiphagocytic poly-D-glutamate capsule.
Figure 5B:
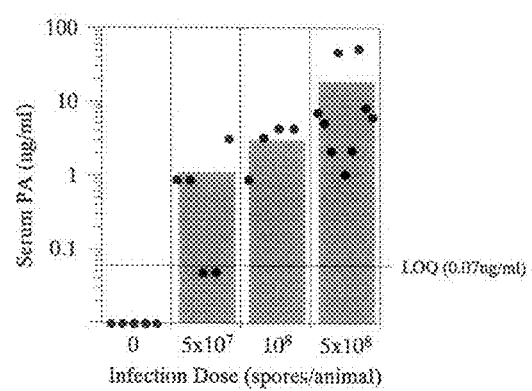

As depicted in FIG. 1A, the genome of *B. anthracis* contains two highly similar ORFs encoding two paralogue proteins (62% amino-acid sequence similarity, sequence coverage 97%, BLAST analysis E value $3e^{-86}$) belonging to the Deg serine protease family: (i) the monocistronic gene specified by the above mentioned locus BA3660, denoted herein as SEQ ID NO: 27, and (ii) the paralogue ORF BA5710, which is the 6$^{th}$ gene in the yycGF operon (FIG. 1A). In analogy to the nomenclature in *B. subtillis*, which expresses the two structurally similar paralogues HtrA and HtrB (Noone et al., 2001), the product of the locus BA3660 is arbitrarily referred to herein as HtrA, and the locus BA5710 is referred to herein as HtrB, (and accordingly, their respective genes are denoted as htrA and htrB, FIG. 1A). In B. subtillis, HtrA and HtrB are co-induced during heat-shock response and concomitantly expressed, fulfilling redundant biological functions. In B. anthracis, while HtrA can be detected as an abundant secreted and membrane-bound protein (for example FIG. 1B and FIG. 2A), HtrB was not detected in any of the cultures investigated in the course of exhaustive proteomic serological screens previously carried out, suggesting that its level of expression is much lower than that of HtrA. The absence of HtrB in the proteome may have been due to silencing of the htrB gene by some mutations in the Vollum isolate that served in these studies. However, the inventors have recently sequenced the whole genome of this Vollum isolate and established that the entire yycGF operon including the htrB genes as well as the intergenic DNA fragment upstream of the operon, are intact. Real time quantitative Reverse Transcriptase-PCR (Q-RT-PCR) analysis clearly confirms that under the conditions tested, htrB specific mRNA levels are at least 20 fold lower than those of htrA (FIG. 1C).

Throughout this specification HtrA designates the protein encoded by the gene BA3660 in all the genomes of *B. anthracis* strains in the NCBI data base. This locus tag refers to the "Ames ancestor" genome which is by consensus used for designation of *B. anthracis* genes.

The *B. anthracis* HtrA protein exhibits 100% identity with its respective paralogues from all members of the *B. cereus* sensu lato group: e.g. *B. cereus* and *B. thuringiensis*.

To gain an insight into the possible role of *B. anthracis* HtrA, the inventors have first generated an htrA mutated *B. anthracis* strain in the background of the avirulent ΔVollum ($pXO1^-/pXO2^-$) strain (designated ΔV, see list of strains used in this study in Table 1). Disruption of the htrA gene (indicated herein as ΔhtrA), resulted in the complete abrogation of HtrA expression (FIG. 2A). Under normal culturing conditions, the mutated and parental strains exhibited indistinguishable growth profiles at 37° C. (FIG. 2B), but as expected from abrogation of the High Temperature Requirement function, the ΔVΔhtrA strain was unable to grow at elevated temperature (e.g. 42° C., FIG. 2C). The observation that in *B. anthracis*, HtrA is critical for growth at elevated temperatures strengthens the notion that its loss of function is not compensated by other redundant proteins in the htrA mutant (note also that levels of htrB mRNA are not affected by the ΔhtrA mutation [FIG. 2D]).

Proteomic Examination of ΔVΔhtrA Secreteomes

In some gram positive bacteria (for example *B. subtilis*, and *Streptococcus pyogenes*) HtrA appears to be an integral part of the secretion apparatus and therefore, the bacterial secretome profile may be expected to change due to the htrA gene-disruption. Accordingly, we conducted a proteomic comparison (by high resolution 2D electrophoresis and subsequent mass-spectrometric identification of differentially expressed proteins) of the secretomes of the *B. anthracis* ΔV and its HtrA disrupted derivative from cultures grown in rich-media (FAG media, FIG. 2E upper panels) and low-nutrient media (NBY, FIG. 2E, lower panels). This analysis established that the secreted proteins mostly affected by the disruption of the htrA gene are the S-layer proteins Sap (locus tag BA885) and EA1 (BA887), and the protein NprA (BA599). Most notably the S-layer proteins and NprA represent very abundant components of the rich and low-nutrient media secretomes, respectively (FIG. 2E).

In addition to these major differences between the proteomes of the parental and the htrA disrupted strain, only minor alterations in the abundance of other extracellular proteins were observed (see FIG. 9).

Sap and EA1 (encoded by the two contiguous chromosomal genes sap and eag) represent major components of the proteinous make-up of the cells and bacterial secretome in vitro, and are expressed in vivo during infection. The physiological role of the *B. anthracis* S-layer in the bacterial expansion in the host is still not fully understood, yet S-layer association (mediated by S layer homology [SLH] domains) may represent a prevalent anchorage modality of exposed proteins on the surface of *B. anthracis*. The observation that Sap and EA1 are completely absent from the supernatant of the rich-medium culture of ΔVΔhtrA strain (FIG. 2E), prompted the inventors to inspect the presence of the S-layer in the cellular fraction as well. Western blot analysis of the cellular fraction of the cells clearly establishes that, as in the case of the secreted fraction, a dramatic decrease in the amount of the S-layer proteins Sap and EA1 characterizes the phenotype of the ΔVΔhtrA strain (FIG. 3A). This decrease is quite remarkable, if one considers the large amounts of S-layer proteins in the cell associated extract (10-30% of protein total, see FIG. 3A, coomassie-blue stained gel in panel 1). Notably, wild-type levels of the S-layer proteins could be restored by expressing HtrA from a transfected plasmid in the trans-complemented strain ΔVΔhtrA/HtrA (slots marked "c" in FIG. 3A). Interestingly, similar amounts of sap and eag message RNA could be detected in the ΔV, and in both the htrA mutated and its transcomplemented strains (FIG. 3C), indicating that the lack of S-layer proteins may not be attributed to repression of transcription due to the mutation in the htrA gene. A complete disappearance of the S-layer was previously observed only when both of the adjacent sap and eag genes were disrupted or in strains in which genes encoding for functions governing the pyruvylation of cell wall polysaccharide were mutated, resulting in the inability of the Sap or EA1 monomers to multimerize and anchor at the bacterial cell-wall. In the latter case, significant amounts of EA1 and Sap were found to be secreted to the culture media suggesting that the S-layer proteins are synthesized and are correctly exported across the cell membrane, yet they fail to be retained on the cell surface. This situation clearly differs from the one that observed in the htrA disrupted mutant, since in this case Sap and EA1 are absent from the cell associated fraction as well as from the media.

An additional protein most strikingly down-regulated in the ΔVΔhtrA cells, is the secreted protease NprA (see Western blot analysis in FIG. 3B). NprA, which represents more than 50% of the total secreted protein mass present in the low-nutrient media of *B. anthracis* parental cells cultures, is undetected in the extracellular fraction as well as the cell-associated fractions of the ΔVΔhtrA strain (FIG. 2E, compare gel 3 and 4; FIG. 3B, gel 8 and blot 10). As in the case of the S-layer proteins, the level of NprA could be fully restored upon trans-complementation in the strain ΔVΔhtrA/HtrA (FIG. 3B, Western blots 9 and 10). But unlike the case of sap and eag the Q-RT-PCR analysis of the nprA gene expression in the parental, htrA-disrupted and HtrA-complemented strains, established that the observed absence of NprA from the ΔhtrA strain cultures is due to a complete shut-off of the nprA gene expression, as attested by the drop in the levels of nprA mRNA to undetectable levels (FIG. 3C, histograms in the right panel).

Disruption of the htrA Gene in the Fully Virulent Vollum Strain and In-Vivo Assessment of the Importance of HtrA for Infection To directly assess the importance of HtrA in *B. anthracis* virulence, an htrA disrupted strain as well as a trans-complemented strain expressing HtrA from a transfected plasmid, were generated in the background of the parental fully virulent Vollum strain containing the native virulence plasmids pXO1 and pXO2. Under in vitro optimal culturing conditions, the VΔhtrA and the corresponding HtrA transcomplemented strains exhibited growth profiles indistinguishable from the parental Vollum strain. Experimental animals were infected sub-coutaneously (SC) with increasing doses of spores of the parental virulent Vollum, the VΔhtrA, and the transcomplemented VΔhtrA/HtrA strains, and their survival was monitored for 14 days (FIG. 4). Remarkably, the animals infected with the VΔhtrA mutant spores, exhibited a dramatic increase in the survival rate compared to the wild-type (WT) parental spores. The estimated $LD_{50}$ (Lethal Dose 50%) of the mutated strain was $\geq 3 \times 10^8$, 6-7 orders of magnitude higher than that calculated for the Vollum spores ($LD50_{WT(SC)} = 10^2$ spores, FIG. 4). Notably, this dramatic diminution of virulence could be restored in the VΔhtrA/HtrA transcomplemented strain, confirming that virulence attenuation is due to the abrogation of HtrA expression in the mutated strain. Experiments in which spores were administrated by the intra-nasal (IN) route of infection, established that inoculation with as many as $10^8$ spores of the V ΔhtrA mutant strain did not affect animal survival, representing an attenuation of at least 4 orders of magnitude. In view of the dramatic affect of htrA disruption on virulence, it was important to determine whether or not the major virulence factors are expressed by the mutated strain. Western blot analyses using anti PA, anti LF and anti EF antibodies, and specific capsule staining (FIG. 5) of $CO_2$-induced cultures, revealed that the htrA mutated strain is indistinguishable from the parental isogenic strain with respect to its ability to express the bacterial toxin and the capsule. The mutated strain could also express PA in vivo, in an infection dose-dependent manner, as directly detected in the circulation of infected animals following SC infection (FIG. 5B). Administration of the VΔhtrA spores resulted in a strong anti-PA humoral response in the infected animals (see hereinbelow) again consistent with the notion that the attenuation characterizing the htrA mutant cells cannot be attributed to an inability to express or secrete the anthrax toxins. It is important to note that such an extent of attenuation of virulence is unprecedented in *B. anthracis* strains which can express both the LT and ET toxins as well as the capsule. Furthermore, the ΔhtrA strain in the Vollum background appears to be even much more attenuated than the noncapsular Sterne pXO2⁻ vaccine strain (FIG. 4). Thus, HtrA appears to be essential for the full manifestation of *B. anthracis* pathogenicity by a mechanism that does not involve the anthrax exotoxins.

In view of the effect of the htrA disruption on the levels of S-layer proteins and NprA, observed in the ΔVΔhtrA strain, expression of these proteins was examined also in the VollumΔhtrA strain (FIG. 10). Western blot analyses established that in contrast to the ΔVΔhtrA, the S-layer protein level is not affected in the V ΔhtrA strain. However, the VΔhtrA cells exhibit a shut-off of the NprA expression, similar to that observed for the ΔVΔhtrA. Both of these observations are in line with the known susceptibility of S-layer protein expression to factors encoded by genes located on pXO1 and the fact that, contrary to the S-layer proteins, NprA belongs to a $CO_2$ shut-off regulon (a group of genes exhibiting similar patterns of expression) dependent solely on chromosome-encoded genes. Apart from the shut-off of NprA in the VΔhtrA strain, proteomic comparison between the parental Vollum and the isogenic ΔhtrA mutant did not reveal any marked difference in the pattern of expression of other proteins other then those reported for ΔVΔhtrA (FIG. 9).

HtrA Mutated *B. Anthracis* Bacteria Exhibit Increased Sensitivity to Stress

To shed some light on the phenotypic characteristics which may be responsible for the remarkable attenuation of the htrA disrupted strain, and considering the known involvement of proteins belonging to the HtrA family in stress response in other bacteria, the inventors have examined the ability of the *B. anthracis* htrA disrupted strains to withstand a variety of stress regimens, compared to the parental virulent WT strains (FIG. 6). The evaluated stress conditions included those known to induce the general stress response in *B. subtillis*: (i) growth in the presence of ethanol (FIG. 6A), (ii) peroxide treatment, which probe the ability of the cells to cope with oxidative stress (FIG. 6B), (iii) growth in the presence of elevated NaCl concentration, which probes osmotic stress (FIG. 6C), and (iv) growth of the bacteria at different temperatures, to assess the tolerance to heat stress (FIG. 6D). In all cases, the growth rates of the V ΔhtrA bacterial cultures were reduced compared to the parental isogenic Vollum strain, while its growth rates in permissive non stress-inducing conditions was indistinguishable from that of the parental strain. In particular, the tolerance to hydrogen peroxide and to heat were dramatically affected by htrA disruption (FIGS. 6B and 6D): the mutated strain was completely blocked in its ability to grow at as low as 0.25 mM $H_2O_2$ or at 42° C., conditions which enabled efficient growth of the wild-type parental strain. These data suggest that HtrA plays an essential role in resilience to stress.

Most notably, in all instances, the reduced growth rate under stress conditions could be fully restored to a wild-type level by expression of HtrA in the trans-complemented strain (FIG. 6), demonstrating that the phenotype can be attributed to the disruption of the htrA locus. It is noteworthy that in *B. anthracis*, the deleterious consequences of HtrA absence do not appear to be masked by any putative compensating functionally redundant proteins. The phenotype of increased sensitivity to stress induced by $H_2O_2$, EtOH and NaCl, as well as the inability to grow at 42° C. were exhibited both by the VΔhtrA and the ΔVΔhtrA strains indicating that presence of both of the two virulence plasmids is not essential for the HtrA-mediated stress tolerance of the bacteria.

Altered Ability of VollumΔhtrA Bacteria to Propagate in Cultured Macrophages

The interaction of *B. anthracis* spores with phagocytic cells is critical in anthrax pathogenesis representing the initial step of infection, required for germination of the spores into toxin producing bacilli and systemic dissemination of the bacteria. Furthermore, the intra-macrophage milieu exerts severe environmental insults, in particular oxidative stress, upon invading micro-organisms, representing a primary anti-bacterial sentinel mechanism. Therefore, in view of the results reported above, the ability of the htrA mutated strain to propagate in phagocytic cells was addressed in the J774.1 murine-macrophage infection assay. This assay monitors the expansion of the bacteria (by viable counting) and lysis of the macrophages (which may be quantified by release into the medium of the intracellular enzyme lactate dehydrogenase [LDH]) following internalization of spores. Typically, *B. anthracis* bacilli can be detected in the supernatant of infected J774.1 cells 4 hours post infection (multiplicity of infection [MOI] 1:5), concomitant with the onset of macrophage lysis. The data depicted in FIG. 7 clearly demonstrates that the appearance of the mutated bacteria in the macrophage supernatant is considerably delayed (10 hours post-infection for the VΔhtrA strain, compared to 4 hours for the Vollum strain, FIG. 7A), as well as the lytic effect that the infection has upon the host cells (90% lysis of the cells infected with the mutated bacteria was observed 25 hours post spore infection, while cells infected with bacteria of the parental strain exhibited significant lysis as early as 8 hours post infection and complete (100%) lysis within less than 18 hours post-infection, FIG. 7B). Of note, the mutated and the parental strains exhibited indistinguishable growth profiles in the macrophage culture medium (FIG. 7A, inset), therefore the observed delay cannot be explained by effects of the medium itself. As in the case of all other phenotypic characteristics associated with the htrA disruption, also the observed delay in propagation in macrophage cell line was fully alleviated in the transcomplemented VΔhtrA/HtrA strain.

The Vollum ΔhtrA Attenuated Spores can Induce Effective Protective Immunity

Given the remarkable attenuation of virulence promoted by htrA-disruption, the inventors have examined whether administration of VΔhtrA spores may confer protective anthrax immunity. To address this issue, the immune status of guinea pigs immunized with ΔhtrA spores was addressed by determining the anti PA humoral response and by a subsequent challenge with fully virulent spores (FIG. 8). All animals immunized with $3\times10^8$ and 80% of the animals administered with $10^8$ V ΔhtrA spores developed relatively high titers of anti-PA antibodies (FIG. 8B, left panel). At the individual animal level, all seroconverted animals exhibited, four weeks post-immunization, anti-PA titers of >800 and anti PA-neutralizing titers between 200-400. Such titers have been previously shown to provide effective protective immunity. Indeed, from a total of 14 animals that seroconverted in the various immunization groups, 13 were protected from a lethal spore challenge ($50\times LD_{50}$ of Vollum). Furthermore, the survival of the animals could be directly related to the immunization dose (FIG. 8B, right panel).

As depicted in FIG. 11A and FIG. 11B, Guinea pigs were immunized with the indicated doses of spores (10 animals per group immunized with $3\times10^7$ and $10^8$; 5 animals in the group immunized with $3\times10^8$ spores). Three out of ten animals immunized with $3\times10^8$ spores survived the immunization. Histograms represent the anti PA titers measured 4 weeks post-immunization in individual animals (left panel; individual animals are identified by numbers under their respective histogram). All animals exhibiting anti-PA antibody titers higher than 200 survived a first challenge with 50 $LD_{50}$ fully virulent Vollum spores. Histograms representing the titers of the animals which survived the challenge are shadowed. All animals that did not survive the challenge are absent from the right panel (boost effect) while all animals which survived the first challenge developed high titers of antibodies and survived a second challenge with 2000 $LD_{50}$ virulent Vollum spores.

The results are consistent with the observation (FIG. 5B) that the bacterial toxins are produced during infection by cells of the mutated strain and establish that the attenuation of virulence does not compromise the ability of the bacteria to convey efficacious protective immunity.

Disruption of the htrA Gene in the Non-Capsular Sterne Strain and In-Vivo Assessment of Virulence of the Sterne ΔhtrA Strain The *B. anthracis* Sterne strain containing only the native virulence plasmids pXO1, was developed more than 60 years ago as a vaccine strain, yet due its toxicity (evidenced by animal experimentation), it does not meet the safety requirements mandated for human use and therefore is accepted in the Western world for veterinary purposes only. Following realization of the importance of HtrA in *B. anthracis* virulence and that HtrA is essential for the full manifestation of *B. anthracis* pathogenicity by a mechanism that does not involve the anthrax exotoxins, an htrA disrupted strain was generated by the inventors also in the background of the Sterne strain, according to the same approach employed for the generation of the htrA disrupted strain in the background of the Vollum strain. The HtrA locus tag in the *B. anthracis* Sterne genome in the NCBI data base is BAS3395. Experimental animals were infected subcoutaneously (SC) with increasing doses of spores of the parental virulent Sterne and the SterneΔhtrA strain and their survival was monitored (FIG. 12A). As demonstrated in the case of the VollumΔhtrA mutant spores (FIG. 4), the animals infected with the SterneΔhtrA mutant spores, exhibited also a dramatic increase in the survival rate compared to the parental Sterne spores. The estimated $LD_{50}$ (Lethal Dose 50%) of the mutated strain was $\geq 10^9$. As in the case of the VΔhtrA, administration of the SterneΔhtrA spores resulted in a potent anti-PA humoral response in the infected animals.

Further, the inventors examined whether administration of SterneΔhtrA spores may confer protective anthrax immunity. To address this issue, the immune status of guinea pigs immunized with ΔhtrA Sterne spores was addressed by determining the anti PA humoral response and by a subsequent challenge with fully virulent spores (FIG. 12B and FIG. 12C). All animals immunized with more than $10^8$ and 80% of the animals administered with $10^7$ SterneΔhtrA spores developed titers of anti-PA antibodies (FIG. 12B). Furthermore, the survival of the animals could be directly related to the immunization dose (FIG. 12C, right panel). The results are consistent with the observation that the bacterial toxins are produced during infection by cells of the mutated strain and establish that the attenuation of virulence does not compromise the ability of the bacteria to convey efficacious protective immunity. The results indicate that the HtrA mutation in the background of the Sterne strain generated a much safer vaccine compared to the parental Sterne strain. Thus, while 100% protective immunity conferred by the parental Sterne strain are achieved by administration of $10^6$ spores (the LD50 value), similar levels of protection are achieved by administration of less than $\frac{1}{100}$ $LD_{50}$ of the SterneΔhtrA spores. This unexpected result indicates that the disruption of htrA represents the basis for the development of an improved vaccine strain exhibiting a significant attenuated phenotype (100 increase in its therapeutic index) suitable both for veterinary and human use.

Use of htrA Disrupted Strains as a Platform for Expression and Protective Immunization with Homologous and Heterologous Bacterial Antigens Having realized that (i) disruption of the htrA gene provides means for generation of *B. anthracis* strains exhibiting protective immunization abilities as well as improved safety, and that (ii) this mutation can be successfully introduced in the Vollum, ΔVollum and Sterne strains resulting in similar phenotypes, the inventors provide evidence that the htrA mutation represents also a more general approach for safety improvement in additional *B. anthracis* derived vaccine strains suitable for prophylaxis of anthrax as well as for other pathogens. Indeed, the inventors have developed in the past a platform strain of B. anthracis based on the ATCC14185 non-encapsulated and non-proteolytic strain, which was further attenuated by curing the plasmid pXO1 which encodes the binary toxin. This strain, designated Δ14185, was used successfully as a platform for expression of recombinant versions of PA, providing long-lasting immunity in guinea-pigs following its administration as spores (Cohen et al., 2000; Gat et al., 2003; Mendelson et al., 2005), see FIG. 13A. These recombinant PA producing spores proved to be (in the guinea pig model) efficacious vaccines by a variety of routes of immunization (s.c., i.m., i.n. and per-os), providing protection against lethal challenge of animals exposed to the pathogen either by subcutaneous or airway infection. Furthermore, using the same expression and immunization system, mice could be immunized with attenuated B. anthracis spores expressing both the PA and the heterologous Yersinia pestis V antigen (FIG. 13B). A strong humoral response could be elicited by administration of these spores, resulting in full protection against a subsequent challenge with either B. anthracis or Y. pestis (FIG. 13C). It should be noted that the term "homologous" as used herein refers to a B. anthracis-derived antigen, and the term "heterologous" refers to an antigen derived from another pathogen. The inventors believed that it is possible to generate similar multivalent vaccines in the background of htrA mutated strains, considering that htrA disruption results in further attenuation without compromising the ability of the bacteria to express the various toxins or derivatives. This issue was examined by over-expressing in the ΔVollumΔhtrA strain a recombinant version of PA using the expression system described in FIG. 13A. The data depicted in FIG. 13D, clearly demonstrate that the htrA mutation did not affect the ability of B. anthracis to express and secrete into the medium recombinant PA. This result was surprising considering the fact that HtrA is a chaperone whose absence may have been expected to influence the ability of the cells to secrete recombinant antigens.

Disruption of the htrA Gene Affects the Levels of the Extracellular NprA Protease and the S-Layer Proteins Sap and EA1

Proteomic analysis of the secretome revealed two major differences between the ΔhtrA mutants and the corresponding Vollum or ΔV parental strains: (i) the complete absence of the extra-cellular protease NprA and (ii) alterations in the expression of the S-layer proteins Sap and EA1 (FIG. 2, FIG. 3 and FIG. 9). Extensive proteomic examination of the htrA disrupted strains, failed to identify similar major alterations in the pattern of expression of other proteins, although some minor effects were noted (FIG. 9). The absence of NprA occurred upon abrogation of HtrA expression, both in the VΔhtrA and the ΔVΔhtrA strains (FIG. 3B and FIG. 10). This observation is in line with the inventor's previous studies showing that the pattern of expression of NprA, the most abundant extracellular protease secreted by B. anthracis under low-nutrient, stress-inducing culturing conditions, depends solely upon chromosomally-encoded $CO_2$-responsive regulatory circuits (Chitlaru et al., 2006, 2010). Interestingly, it was shown that under nutrient deprivation conditions, in the closely phylogenetically-related bacterium B. cereus, NprA may be involved in a cell-cell communication quorum sensing mechanism. The complete silencing of the NprA gene in the HtrA mutated strains may suggest that HtrA is involved also in the response to starvation, in good agreement with the role that HtrA may have in allowing the bacterial cells to tolerate a variety of environmental insults.

It should be noted that it is quite unlikely that the shut-off of the NprA gene in the HtrA mutants is involved in the virulence attenuation of the mutated strain. This conclusion is supported by the following considerations: (i) under conditions in which the anthrax toxins are induced, NprA is repressed, probably due to its ability to cleave proteolytically essential virulence factors (Chitlaru et al., 2006, 2010) and (ii) NprA is not expressed in vivo as evidenced by the lack of anti NprA antibodies in a wide repertoire of sera collected from experimentally infected animals, in spite of the fact that by itself, purified NprA is a potent immunogen (Chitlaru et al., 2007).

Figure 2E:
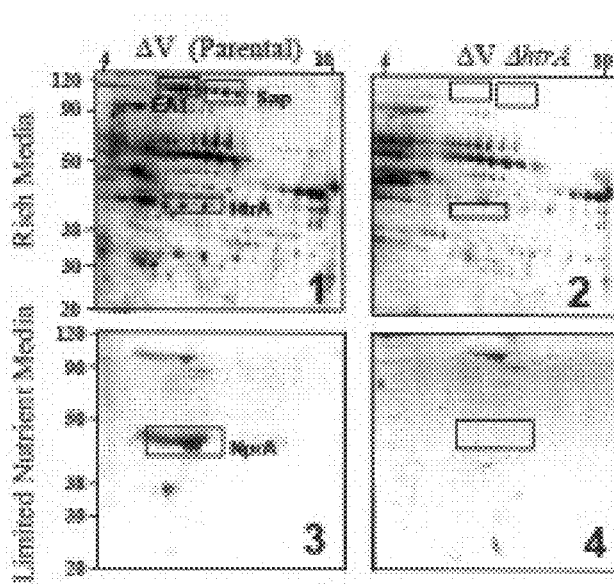

Two additional proteins are profoundly affected by the HtrA null mutation; these are the S-layer proteins Sap and EA1. Strikingly, Sap and EA1 are absent both from the surface and the secreted fraction of the htrA disrupted strain (FIGS. 2E and 3A), an effect which is worth-noting considering that the S-layer proteins are the most abundant B. anthracis proteins and may represent sometimes as much as 70% of the total proteinous mass of the bacterial surface (Chitlaru et al., 2004). Yet, this silencing effect is observed only in the ΔV htrA disrupted strain which is cured of the pXO1 and pXO2 (FIG. 2E and FIG. 10). Since a decrease in the level of S-layer did not occur in the htrA disrupted strain generated in the background of the virulent Vollum strain, it is conceivable to conclude that expression of S-layer is governed by at least two converging regulatory pathways: one involves the product of pXO1-located factors, as documented in the past, and a second post-transcriptionally regulatory pathway, involving the chromosomally encoded HtrA, as evidenced in the present invention. Interference with both pathways, as is the case for htrA disruption in the pXO1 and pXO2 devoid strain, may therefore result in the absence of the S-layer. It is interesting to note that HtrA-promoted post-transcriptional modulation of abundant proteins, was already recorded in Streptococcus pneumoniae, suggesting that interference with regulatory pathways may represent a more universal activity exerted by HtrA.

HtrA is Essential for Manifestation of B. Anthracis Virulence Possibly Due to its Role in Resilience to Stress A major observation of the present invention is the dramatic decrease in virulence caused by disruption of the htrA gene (FIG. 4). The virulence of the ΔhtrA strain in guinea pigs is at least 6 orders of magnitude lower following sub-cutaneous administration ($LD_{50}$>3×10$^8$ spores) and at least 4 orders of magnitude lower following intranasal infection. Interestingly, the htrA disrupted cells are even more attenuated in the guinea pig model than bacteria of the non-capsulated Sterne vaccine strain (devoid of the pXO2 plasmid; $LD_{50}$Sterne=5×10$^6$, FIG. 4). Notably, the ΔhtrA strain are clearly shown to express the bacterial toxin and capsule in vitro; PA can be detected in the circulation of infected animals and anti PA antibodies are efficiently elicited in these animals, demonstrating that the toxin can also be expressed in vivo during infection (FIG. 5 and FIG. 8). The results of the present invention suggest that the marked attenuation following disruption of the htrA gene is due to the low resilience of the mutated cells to a variety of stress conditions (FIG. 6). This low resilience may explain also the observed effect that the mutation has on the ability of the bacteria to propagate in the J774.1 macrophage line (FIG. 7). The increased sensitivity to stress is manifested independent of the virulence plasmids, as indicated by the observation that the ΔVΔhtrA and VΔhtrA strains exhibit indistinguishable increased stress susceptibility. Thus, the stress regulon of B. anthracis appears to be governed by chromosomally located genes. While pXO1 and pXO2-encoded regulatory factors are essential for expression of the toxin, they are apparently dispensable for proper HtrA-dependent tolerance to stress regimens.

In *Bacillus subtillis* there are 3 monocistronic genes encoding HtrA homologous proteins (ykdA, yvtA and yyxA). HtrA—the product of ykdA and HtrB-encoded by yvtA, are highly similar proteins activated by the CssRS two-component system which senses accumulation of misfolded proteins at the membrane cell interface (Noone et al., 2001); furthermore, HtrA and HtrB may mutually compensate each other in mutated *B. subtilis* strains. In *B. anthracis*, a paralogue htrB gene is located on the yycGF operon (see FIG. 1), an operon which in *B. subtillis* was invoked in stress response (Dubrac et al., 2008). Based on this chromosomal location, one could have expected that HtrB in *B. anthracis* would also be expressed, yet only HtrA was detected in previous proteomic studies of *B. anthracis* vegetative cultures (FIGS. 1B and 1C). These results are in line with previous extensive micro-array-based transcriptomics studies of *B. anthracis* cultured under sporulating conditions, which indicated that HtrA and HtrB are expressed in two complete different growth phases: while HtrA RNA transcripts were detected in the logarithmic and transition stages, HtrB transcripts could be detected only in a very late stationary phase preceding the final stage of sporulation and the HtrB protein was detected in the endospore. These studies indicate that HtrA and HtrB exhibit profoundly different patterns of expression and strongly suggest that they do not fulfill redundant physiological functions. In the results presented herein, it is evident that silencing of HtrA by targeted disruption of the htrA gene is not accompanied by a compensatory elevation in the expression of HtrB (FIG. 2D) and accordingly, the *B. anthracis* ΔhtrA strains exhibit the observed reduction in their ability to tolerate stress (FIG. 6). In this respect, *B. anthracis* seems to be more similar to various human pathogens such as Streptococci (*S. mutans, pyogenes* and *S. pneumoniae*) or to *Lactococcus lactis*, where htrA genes are functionally non-redundant, rather than with the phylogenetically-closer *B. subtilis*.

The role of HtrA in the virulence of other pathogens was suggested to reflect one or a combination of the following phenomena: (i) involvement in the processing/secretion of virulence factors; (ii) interaction with some host elements, as was recently described for *Helicobacter pylori* HtrA and other bacterial proteases which digest host tissue or immune effectors; (iii) HtrA has an important role in stress response, which in turn is responsible for the survival of the bacteria during infection (see examples in Streptococci, *Yersinia, Salmonella typhimurium*). In the case of *B. anthracis*, one cannot rule out that HtrA is necessary during infection for proteolysis of host proteins. Such a role is compatible with the fact that, in addition of its membranal localization that would be required for its function in secretion and processing of mal-folded polypeptides, HtrA is one of the most abundant extracellular protease secreted by *B. anthracis* under conditions mimicking infection (Chitlaru et al., 2006, 2010) as well as early during infection (Sela Abramovich et al., 2009). In this context, it is worth noting the HtrA-dependent effects on proteolysis of the putative LytE extracellular protein (see FIG. 9, comment c). Yet, the studies documented here clearly indicate that the most plausible explanation for the remarkable attenuation of the disrupted strain relates to its limited ability to withstand environmental insults that the bacteria may encounter in the host. It is quite remarkable and unexpected that a single unique protein with such a pivotal role in pathogenesis and virulence, appears to lack any compensatory "back-up" functional paralogues, as for example was recently demonstrated in the case of the multiple superoxid dismutases (SOD) proteins active in protection of *B. anthracis* spores from oxidative stress.

It is important to stress that the extent of virulence attenuation associated with htrA disruption is significantly higher than that promoted by disruption of any other reported *B. anthracis* virulence factors assessed in murine or guinea pig models of anthrax. In view of its essential nature, HtrA represents the basis for the development of novel therapeutic interventions to countermeasure *B. anthracis* infection.

In certain embodiments, provided is the use of a *B. anthracis* mutant deficient in HtrA expression in a vaccine. The vaccine according to the present invention is suitable and effective both for pre- and post-exposure prophylaxis.

It should be noted that any reference herein to the disruption of the HtrA gene refers to a full or partial disruption of the gene by the removal of the entire HtrA gene or any part thereof or any mutation therein by any known recombinant techniques such as, for example, homologous recombination, transposon mutagenesis, and others, wherein deletions, insertions or (point) mutations are introduced in the genome.

Furthermore, the present invention demonstrates that the HtrA mutation represents a means by which an improved live attenuated vaccine strain for *B. anthracis* prevention can be developed.

A specific embodiment of the present invention provides the use of attenuated *B. anthracis* cells in the expression of various antigens, including heterologous antigens. As shown in FIG. 13, upon disruption of the htrA gene, the ability of the cells to express these heterologous antigens is not affected. Taken together, the data presented herein provides evidence that the htrA mutated *B. anthracis* strain can serve as a platform for delivery of antigens, which results in manifestation of their protective ability and thus, the engineered bacteria have an important potential as vaccination vehicles against *B. anthracis* as well as other pathogens.

Examples

Experimental Procedures

Bacterial Strains, Media, Growth Conditions and Stress Treatments

Bacterial strains, plasmids, and primers used herein are listed in Table 1 and 2 below. The *B. anthracis* strains used are the fully virulent Vollum strain (pXO1$^+$; pXO2$^+$, denoted V), its derivative—the attenuated strains Vollum (pXO1$^-$; pXO2$^-$, denoted ΔV), and ΔhtrA strains generated in either V or ΔV (Table 1), as well as their corresponding trans-complementation strains (designated VΔhtrA/HtrA and ΔVΔhtrA/HtrA, respectively). Cells were cultured either in FAG media (Cohen et al., 2000), Brain-Heart Infusion (BHI, DIFCO/Becton Dickinson, MD, USA) or NBY low-nutrient content media (0.8% [w/vol] Nutrient Broth [Difco], 0.3% Yeast extract [Difco] and 0.5% Glucose) for up to 24 hours at 37° C. with vigorous agitation. For identification of $CO_2$-induced proteins, cells were grown at 37° C. in NBY supplemented with 0.9% $NaHCO_3$ in hermetically-sealed filled-up flasks, without agitation (referred hereafter as NBY—$CO_2$). NBY—$CO_2$ media promotes very efficient toxin production and capsule synthesis (which can be visualized by negative staining using India ink [Becton Dickinson, MD, USA]). Spores were prepared in Schaeffer's sporulation media at 34° C. for 72 hours vigorously shaken, as described in Cohen et al., 2000. In all cases, cultures were initiated with a fresh starter inoculum diluted to a final OD of 0.1 in the respective media. For examination of the ability of the cells to tolerate various stress regimens, the cells were allowed to grow under optimal conditions for 2.5-3 hours (typically the time needed to enter logarithmic phase), then split into BHI cultures containing the indicated final concentrations of $H_2O_2$, EtOH or NaCl, or pre-heated at the indicated temperatures. The growth rate μ (expressed in $hr^{-1}$) was calculated as $60\times[\ln(OD_2/OD_1)]/(t_2-t_1)$ where $OD_1$ and $OD_2$ are the optical densities measured at two time-points ($t_1$ and $t_2$ expressed in minutes) along the logarithmic growth phase.

*Escherichia coli* strains (Table 1) were used for plasmid construction. Antibiotic concentrations used for selection in Luria-Bertani (LB, Difco) agar/broth were: for *E. coli* strains, ampicillin (Ap, 100 μg $ml^{-1}$), for *B. anthracis* strains, kanamycin (Km, 10 μg $ml^{-1}$), chloramphenicol (Cm, 7.5 μg $ml^{-1}$) and erythromycin (Em, 5 μg $ml^{-1}$).

Two-Dimensional Electrophoresis (2-DE) Separation and MS Identification of Secreted Proteins Secreted proteins were collected from the indicated media and subjected to proteomic 2-DE analysis essentially as described in Chitlaru et al., 2006. In brief, secreted proteins were collected from filtered culture media by overnight precipitation in 10% ice-cold TCA and resuspended in a IEF (isoelectric focusing) solution composed of 8M urea, 4% (w/v) 3-[(3-Cholamidopropyl)dimethylammonio]-1-propanesulfonate (CHAPS), 40 mM Tris, 2% Dithiothreitol (DTT) and 0.2 (w/v) Bio-Lyte 3/10 (BioRad). 200 μg total protein were resolved first by IEF on ready-made 17 cm, immobilized pH gradient (IPG) strips (Immobiline DryStrips, Pharmacia), applied to a Protean IEF cell (Bio-Rad). Electrophoretic separation on the second dimension was performed on 12.5% SDS-PAGE on an Ettan DALT II System (Pharmacia). Gels were stained with G-250 Coomassie blue (Bio-safe, BioRad) and spots detected and analyzed by scanning on a GS-800 Calibrated Densitometer assisted by the PDQuest 2-D Software (BioRad). Protein spots were cut from the 2-DE gels and subjected to in-gel overnight digestion with 6.25 μg $ml^{-1}$ trypsin (Promega). Peptides were eluted with 1% TFA followed by 50% $CH_3CN$, dried and resuspended in 10 μl of 25% $CH_3CN$, 0.1% TFA. Two μl were mixed with an equal volume of a α-cyano matrix (Sigma) and applied to a MALDI-TOF (Matrix Assisted Laser Disorption Ionization-Time of Flight) target. Mass spectra were acquired on a TofSpec 2E apparatus (Micromass) in positive ion reflectron mode. Spectra were compared to theoretical tryptic digest fragments of the genomic sequence of the *B. anthracis* Ames ancestor genome. Identification of proteins was based on a peptide-coverage of more than 30% and peptide mass deviation between observed and calculated values of less than 100 ppm. Identity of all proteins listed in FIG. 9 was confirmed by LC-ESI-MS/MS (Liquid Chromatography Electrospray Ionisation Mass-Spectrometry/Mass) amino-acid sequencing at the proteomic analysis core facility of the Weizmann Institute Biological Services Unit (Weizmann Institute of Science, Rehovot, Israel). Sequenced tryptic peptides, typically represented a coverage>70% of the amino-acid sequence of the analysed protein. Throughout the text, chromosomal ORFs are referred according to the NCBI locus-tag identifier of the *B. anthracis* Ames-ancestor chromosome. Accession numbers of the Ames ancestor genome is NC_007530.

Plasmid and Strain Construction

Plasmids and oligonucleotide primers used in this study are summarized in Tables 1 and 2.

The oligonucleotide primers were designed according to the genomic sequence of *B. anthracis* Ames strain, and prepared using the Expedite synthesizer (Applied Biosystems).

Genomic DNA (containing the chromosomal DNA and the native plasmids, pXO1 and pXO2) was extracted from the Vollum strain, as described in Gat et al., 2008.

PCR amplifications were performed using the Taq (Qiagen) or Expand High Fidelity (Roche) systems.

DNA sequences were determined with the ABI rhodamine termination reaction kit (ABI310 Genetic Analyzer, Applied Biosystems).

For generation of specific anti-HtrA antibodies via DNA immunization, the plasmid pCI-htrA was constructed. Primers HTRA7 (forward) and HTRA8C (reverse) were used to amplify the htrA gene, excluding the 175-bp predicted leader sequence. The PCR product was digested with KpnI and NotI, and cloned in the eukaryotic expression vector pCI, carrying both the T7 promoter for in vitro expression and the eukaryotic cytomegalovirus promoter, for in vivo expression. Large-scale production of pCI-htrA for DNA immunization by gene gun was performed by alkali lysis followed by CsCl gradient centrifugation.

The vector used for disruption of the htrA gene by allelic replacement, pEO-htrA (Table 1), was constructed as follows:

(i) A $Km^R$ gene from pDG782 was inserted as a blunt-ended StuI-SmaI 1.5 kb cassette into the StuI site of pEO.

(ii) Into the vector from step i, a NotI-SpeI 526-bp restriction fragment of the htrA 5' end derived by PCR using HTRA1 (forward) and HTRA2C (reverse) primers, was cloned.

(iii) Finally, a SalI-AscI 512-bp restriction fragment of the htrA 3' end-derived PCR product (HTRA3 and HTRA4C) was introduced.

For the complementation plasmid pASC-HtrA, the htrA complete gene was cloned as a SnaBI/BamHI-digest of PCR product (HTRA5 and HTRA6C primers), replacing the pagA gene in the previously described vector pASC-α (Cohen et al., 2000).

All plasmids transformed into the Vollum strain were first propagated in a methylation deficient *E. coli* strain GM2929 (Table 1). *B. anthracis* cells were electrotransformed as described in Cohen et al., 2000.

To disrupt the htrA gene by homologous recombination, an allelic exchange technique was performed as follows: plasmid pEO-htrA was introduced into competent cells of the Vollum or ΔVollum strains and transformants were selected for $Km^R$ at 30° C. Integrants were recovered by growing transformants in LB broth at 30° C. for 1.5 h, shifting to 38° C. (non-permissive temperature) for 6 h, and then plating serial dilutions on LB plates containing Km, incubated at 38° C. for 12-16 h. Single colonies were selected, resuspended in 0.1 ml LB broth and spotted (5 μl) on LB plates containing Km or Em, then incubated at 42° C. for 12-16 h. Deletion mutants were isolated as $Km^R$ $Em^S$ clones. The deletion of the internal fragment of htrA and insertion of the $Km^R$ cassette into the chromosome were confirmed by PCR using flanking chromosomal primers and primers derived from the Km cassette (primers used: HTRA9/KANA2C and KANA1/HTRA12C for the up-stream and down-stream integration htrA/Km junctions, respectively).

Complementation was accomplished by transforming pHtrA into the htrA mutant strain. The expression of HtrA was verified by Western blot analysis. Correction of the htrA-disruption phenotype by transcomplementation with the plasmid-expressed HtrA, confirms the predicted non-polar nature of the gene-disruption procedure.

TABLE 1

Bacterial strains and plasmids used herein

| Strain | Description | Designation | Source |
|---|---|---|---|
| *B. anthracis* | | | |
| Vollum | Parental (wt) strain. PA$^+$LF$^+$EF$^+$(pXO1$^+$) Cap$^+$(pXO2) | V | ATCC1457 |
| ΔVollum | Vollum cured of both virulence plasmids. PA$^-$LF$^-$EF$^-$(pXO1$^-$) Cap$^-$(pXO2) | ΔV | IIBR stock |
| ΔhtrAVollum | htrA nonpolar delition mutant of Vollum | VΔhtrA | This study |
| ΔhtrAΔVollum | ΔhtrA nonpolar delition mutant of ΔVollum | ΔVΔhtrA | This study |
| ΔhtrAVollum/pHtrA | Complementation of ΔhtrA by htrA expression in trans, from pASC-HtrA | VΔhtrA/HtrA | This study |
| ΔhtrAΔVollum/pHtrA | Complementation of ΔhtrA by htrA expression in trans, from pASC-HtrA | ΔVΔhtrA/HtrA | This study |
| Sterne | Parental (wt) strain. PA$^+$LF$^+$EF$^+$(pXO1$^+$) Cap$^-$(pXO2$^-$) | Sterne | IIBR collection |
| ΔhtrASterne | ΔhtrA nonpolar delition mutant of Sterne | SterneΔhtrA | This study |
| *E. coli* | | | |
| DH5α | endA1 recA1 | | Clontech |
| GM2929 | Dam13::Tn9(Cm$^R$) dcm-6 | | NEB |

| Plasmid | Characteristics | Source |
|---|---|---|
| pCI | *E. coli* -eukaryotic shuttle vector for DNA immunization. Ap$^R$ | Promega |
| pDG782 | Source of Km$^R$ gene | BGSC |
| pCI-htrA | pCI containing a PCR-amplified htrA, without the leader sequence, downstream of T7 and CMV promoters | This study |
| pEO | *B. anthracis* allelic replacement suicide vector. *E. coli*/*Bacillus* shuttle vector. A derivative of pHV1249. Contains the pBR322 ori and the pE194tsori. Ap$^R$Em$^R$ | Gat et al., 2005, 2008 |
| pEO-htrA | pEO containing the KmR gene from pDG782 flanked by two PCR amplified htrA fragments (nucleotides 8 to 533 and 727 to 1238). Used for disruption of htrA | This study |
| pGwt$_{amy}$ | Source of *B. amyloliquifaciens* α-amilase promoter and *B. anthracis* pagA ribosome binding site | Gat et al., 2003 |
| pASC-α | *E. coli*-*Bacillus* expression vector, carrying the pagA gene. Ap$^R$Cm$^R$ pC194ori | Cohen et al., 2000 |
| pASC-HtrA | HtrA expression vector. pASC-α containing a PCR amplified htrA gene replacing the pagA gene, downstream of the pagA ribosome binding site and the α-amylase promoter | This study |

TABLE 2

Primers used herein and their SEQ ID NOs.

| SEQ ID NO. | Primers* | Sequence (5'→3')** | Use |
|---|---|---|---|
| 1 | EAI1 | TGACGTAGGCGAAGGTACAGTTC | Q-RT-PCR of eag |
| 2 | EAI2C | AACGTTACCCTCTGTTACGTTCACA | |
| 3 | GRO1 | TCTTAACTGGTGGCGAAGTAATCA | Q-RT-PCR of groEL |
| 4 | GRO2C | CTTTACCAGCGCGTCCTAAAGAT | |
| 5 | GRO3 | GAAGGTGACGAAGCAACAGGTATC | |
| 6 | GRO4C | CTAGACCAGCGTTGATTGCGA | |
| 7 | HTRA1 | GGGGAAGTAAAgcggccgcATTACGACGGACCAAATTT | Construction of pEO-htrA (NotI) |
| 8 | HTRA2C | CATTAGCACCATactagtCAACAACAGCTAAATCTAAC | Construction of pEO-htrA (SpeI) |
| 9 | HTRA3 | GCAGATTGGAATgtcgacGTTATTCAAACAGATGCAGC | Construction of pEO-htrA (SalI) |
| 10 | HTRA4C | CTTTCTTTTATTggcgcgccTGATTCTTTGTAGCTGAG | Construction of pEO-htrA (AscI) |

TABLE 2-continued

Primers used herein and their SEQ ID NOs.

| SEQ ID NO. | Primers* | Sequence (5'→3')** | Use |
|---|---|---|---|
| 11 | HTRA5 | AGACCTAGATCTTATACAAAAAGGA GtacgtaTATGGGATATTACGACGGACCA | Construction of pASC-HtrA (SnaBI) |
| 12 | HTRA6C | AGATAGACCTGAggatccTTATTGATTCT TTGTAGCTGAGTTATCT | Construction of pASC-HtrA (BamHI) |
| 13 | HTRA7 | CGGAGAATTCTAATACGACTCACTATAggt accACCATGACTGTATCATCTTTTAGTTCA GATTCAAAAG | Construction of pCI-htrA (KpnI) |
| 14 | HTRA8C | GAAGATCTgcggccgcCCGGGTTATTGATTC TTTGTAGCTGAGTTATCTG | Construction of pCI-htrA (NotI) |
| 15 | HTRA9 | CAAGAAGGACACAAAACGTGACTATAC | Confirmation of ΔhtrA by PCR |
| 16 | HTRA10C | GTATAGCCGATAAAGAAAGTCTC | |
| 17 | HTRA11 | AAATTCCAGTAGATATCGATGGCG | Q-RT-PCR of htrA |
| 18 | HTRA12C | TAACGCACCACCACTGTTCC | |
| 19 | HTRB1 | AAATGATACGGGCGCACTTC | Q-TR-PCR of htrB |
| 20 | HTRB2C | CACGATCAACAGCATCCACAA | |
| 21 | KANA1 | GAAGGAATGTCTCCTGCTAAGG | Confirmation of ΔhtrA by PCR |
| 22 | KANA2C | CTGATCGACCGGACGCAGAAG | |
| 23 | NPRA1 | CGCGGAGCAACGATTTTC | Q-RT-PCR of nprA |
| 24 | NPRA2C | ATCATACGCTGCATTGAAAACATT | |
| 25 | SAP1 | TCGAAATGGCTGACCAAACAG | Q-RT-PCR of sap |
| 26 | SAP2C | ACCCTCTGGTGAAACAACTTCAGT | |

*Primers are alphabetically ordered
**When applicable, restriction sites used for cloning are marked in lower-case letters and indicated in the "Use" column, in parantheses.

RNA Isolation and Real Time qRT-PCR (Quantitative Reverse Transcriptase PCR) Analyses Total RNA was extracted from bacteria grown for 6 hours (early stationary), using the RiboPure™-Bacteria Kit (Ambion). Contaminating genomic DNA was removed by DNase treatment according to manufacturer's instructions. RNA was quantified spectrophotometrically, and its integrity was examined by Agarose gel electrophoresis. cDNA was generated with Omniscript™ reverse transcriptase (Qiagen), 10 mM of Random Primers 9 (BioLabs) and 500 ng of RNA. Decimal dilutions (1:10, 1:100) of the cDNA preparations were amplified in triplicated experimental groups using 500 nM gene specific primers, 5 mM Magnesium, 0.25 mM dNTP, Manufacturer-supplied PCR buffer, 100 nM Super ROX (BioSearch technologies), AmpliTaq Gold® DNA polymerase (Applied Biosystems) and EVA green (Biotium Inc).

Experiments were repeated three times for each gene analysed using the 7500 ABI Real Time PCR System (Applied Biosystems). Plasmid DNA containing the analysed gene or standard chromosomal spore DNA (10-10,000 copies/reaction) served as a reference for cDNA quantification. In all cases, control groups using the products of mock reverse transcriptase reactions (no reverse transcriptase), served for determining possible chromosomal DNA contaminations. The values determined in these groups, typically representing less than 5% of the total copies measured, were substracted from the final expression value.

Primers were selected using the Primer Express software (ABI). The following primer combinations were used (Table 2): EAI1/EAI2C for determining expression of eag; GRO1/GRO2C and GRO3/GRO4C for groEL; HTRA11/HTRA12C for htrA; HTRB1 and HTRB2C for htrB; NPRA1/NPRA2C for nprA; SAP1/SAP2C for sap.

SDS-PAGE, Western Blot Analyses, Antibodies, and ELISA

Regular 1-dimensional SDS-PAGE was carried out on 4-12% NuPAGE® Bis-Tris gels (Invitrogen) using Precision Plus Molecular weight markers (Bio-Rad). Western blots were generated using the Nitrocellulose Western iBlot Gel Transfer Semi-dry system (Invitrogen). Visualisation of immunoreactive bands was carried out by an ECL (electro-chemo-luminescence) reaction (Pierce SuperSignal® West Pico Chemiluminescent substrate kit, Thermo Scientific) mediated by peroxidase-conjugated secondary antibodies (Amersham) and detected by the FUJIFILM LAS-3000 detection system.

The following antibodies were used in this study:
(i) Specific anti-HtrA antibodies, obtained by DNA immunization with the pCI-htrA plasmid in female outbred ICR mice, using the Helios Gene Gun System (Bio-Rad), as described by Gat et al., 2007;
(ii) Antibodies recognizing the S-layer proteins Sap or EA1 were kindly provided by Dr. E. Elhanany from IIBR. These specific anti-SLH antibodies, were generated by vaccination of NZW female rabbits with a synthetic peptide representing an epitope from the SLH (S-layer homology) N-terminal domain present in Sap and EA1 proteins.

All other antibodies were previously described:
(iii) Mouse anti-NprA (Chitlaru et al., 2006);
(iv) Rabbit anti-PA antibodies (Gat et al., 2003);
(v) Anti LF; and
(vi) anti-EF mouse (Cohen et al., 2000).

Primary and secondary antibodies were used at 1:1000 and 1:5000 dilutions, respectively.

ELISA tests for quantification of PA in sera samples and detection of anti-PA antibodies in the serum of infected animals were carried out as described previously (Cohen et al., 2000).

Macrophage Infection Assay

Infection of macrophages was carried out as previously described (Gat et al., 2005; Weiss et al., 2009). In brief, murine macrophages of the J774.1 line, grown in DMEM supplemented with 10% fetal calf serum (37° C.; 5% $CO_2$ atmosphere) were seeded at a concentration of $10^5$ cells/well in a 24-wells plate, one day prior to infection. Cells were incubated for 1 hour in the presence of $5 \times 10^5$ B. anthracis spores/well, washed extensively with DMEM supplemented with 2.5 µg/ml gentamycin and incubated for 3 hours in the presence of 2.5 µg/ml gentamycin, washed again and layered with fresh media. Under these conditions, essentially all bacteria which are not internalized in the cells are removed. Supernatants from identically treated wells were harvested at various time points and subjected to viable counting of bacteria emerging from the infected macrophages. Macrophage lysis paralleling the multiplication of the bacteria in the culture was monitored by assaying the accumulated lactate dehydrogenase (LDH) released in the media from the damaged cells at the harvesting times, using a standard LDH-L kit (Thermo-Fisher Scientific, Middletown, Va., USA).

Infection of Guinea Pigs

Female Hartley guinea pigs (Charles River Laboratories), weighting 220 to 250 g, were infected with spore preparations of the mutant or trans-complemented strains and compared with the parental Vollum strain. Prior to infecting the animals, the spore preparations were heat-shocked (70° C., 20 min.) to kill residual vegetative bacteria and serially diluted 10-fold in saline, to produce spore suspensions within the range $10^2$-$10^9$ per ml. A 0.1 ml spore dose volume was administered subcutaneously (s.c.) to each guinea pig. 5-10 guinea pigs per dose-strain were used. The remaining spore dose suspensions were plated for total viable counts (CFU $ml^{-1}$). 24-48 hours post infection, animals were bled by cardiac puncture for determination of the levels of PA in peripheral circulation. The animals were observed daily for 21 days. Four weeks post-infection, surviving animals were bled by cardiac puncture for serological studies.

In immunization experiments, 6 weeks post-infection, animals were challenged s.c. with the indicated lethal dose of the parental *B. anthracis* Vollum strain ($LD_{50}$=100 spores). The spore lethal dose required to kill 50% ($LD_{50}$) of the animals was calculated by the method of Reed and Muench (Reed & Muench, 1938).

Animal experiments were approved by the IIBR committee for animal research (protocol GP-10-2010). Experimental animals were handled according to the National Research Council 1996 Guide for the Care and Use of Laboratory Animals and regulations of the IIBR Animal Use Committee.

Although embodiments of the invention have been described by way of illustration, it will be understood that the invention may be carried out with many variations, modifications, and adaptations, without exceeding the scope of the claims.

BIBLIOGRAPHY

Chitlaru, T., Gat, O., Gozlan, Y., Ariel, N., and Shafferman, A. (2006) Differential proteomic analysis of the *Bacillus anthracis* secretome: distinct plasmid and chromosome $CO_2$-dependent cross-talk mechanisms modulate extracellular proteolytic activities. *J Bacteriol* 188: 3551-3571.

Chitlaru, T., Gat, O., Gozlan, Y., Grosfeld, H., Inbar, I., and Shafferman, A. (2007) Identification of in vivo expressed immunogenic proteins by serological proteome analysis of *Bacillus anthracis* secretome. *Infect Immun* 75: 2841-2852

Chitlaru, T., and Shafferman, A. (2009) Proteomic studies of *Bacillus anthracis*. *Future Microbiol* 4: 983-998.

Chitlaru, T., Gat, O., Zaide, G., Grosfeld, H, Inbar, I., Ehrlich, S., et al. (2010) Proteomic studies of *B. anthracis* reveal in-vitro $CO_2$-Modulation and expression during infection of extracellular proteases. In *The Challenge of Highly Pathogenic Microorganisms, Mechanisms of Virulence and Novel Medical Countermeasures*. Shafferman A, Velan, B., Ordentlich, A., eds. Netherland: Springer, pp. 11-22.

Chitlaru, T., Altboum, Z., Reuveny, S., and Shafferman, A. (2011) Progress and novel strategies in vaccine development and treatment of anthrax. *Immunological Reviews* 239: 221-236.

Cohen, S., Mendelson, I., Altboum, Z., Kobiler, D., Elhanany, E., Bino, T., et al. (2000) Attenuated nontoxinogenic and nonencapsulated recombinant *Bacillus anthracis* spore vaccines protect against anthrax. *Infect Immun* 68: 4549-4558.

Gat, O., Inbar, I., Aloni-Grinstein, R., Zahavy, E., Kronman, C., Mendelson, I., et al. (2003) Use of a promoter trap system in *Bacillus anthracis* and *Bacillus subtilis* for the development of recombinant protective antigen-based vaccines. *Infect Immun* 71:801-813.

Gat, O., Mendelson, I., Chitlaru, T., Ariel, N., Altboum, Z., Levy, H., et al. (2005) The solute-binding component of a putative Mn(II) ABC transporter (MntA) is a novel *Bacillus anthracis* virulence determinant. *Molec Microbiol* 58: 533-551.

Gat, O., Grosfeld, H., Ariel, N., Inbar, I., Zaide, G., Broder, I. et al. (2006) Search for *Bacillus anthracis* potential vaccine candidates by a functional genomic-serologic screen. *Infect Immun* 74: 3987-4001.

Gat, O., Zaide, G., Inbar, I., Grosfeld, H., Chitlaru, T., Levy, H., and Shafferman, A. (2008) Characterization of *Bacillus anthracis* iron-regulated surface determinant (Isd) proteins containing NEAT domains *Molec Microbiol* 70: 983-999.

Mendelson, I., Gat, O., Aloni-Grinstein, R., Altboum, Z., Inbar, I., Kronman, C., et al. (2005) Efficacious, nontoxigenic *Bacillus anthracis* spore vaccines based on strains expressing mutant variants of lethal toxin components. *Vaccine* 23:5688-5697 Reed, L. J., and Muench, H. (1938) A simple method of estimating fifty percent endpoints. *Am J Hyg* 27:493-497.

Noone, D., Howell, A., Collery, R., and Devine, K. M. (2001) YkdA and YvtA, HtrA-like serine proteases in *Bacillus subtillis* engage in negative autoregulation and reciprocal cross-regulation of ykdA and yvtA gene expression. *J Bacteriol* 183: 654-663.

Rasko et al., Nucleic acids research 2004, 32:977-988

Sela-Abramovich, S., Chitlaru, T., Gat, O., Grosfeld, H., Cohen, O. and Shafferman, A. (2009) Novel and Unique Diagnostic Biomarkers for *Bacillus anthracis* Infection. *Applied and Environmental Microbiology* 75: 6157-6167.

Shafferman, A., Gat, O., Ariel, N., Chitlaru, T., Grosfeld, H., Zvi, A., et al. (2010) Reverse Vaccinology in *B. anthracis*. In *The Challenge of Highly Pathogenic Microorganisms, Mechanisms of Virulence and Novel Medical Countermeasures*. Shafferman A, Velan, B., Ordentlich, A., (eds). Netherland: Springer, pp. 295-306.

WO 2010/109451

The invention claimed is:

1. A vaccine for the prophylaxis of anthrax infection comprising a therapeutically effective amount of a live attenuated *Bacillus anthracis* (*B. anthracis*) strain selected from the *B. anthracis* Vollum strain and the *B. anthracis* Sterne strain in which the htrA gene is disrupted by mutation and its expression abrogated, expressing a recombinant homologous or heterologous antigen.

2. A method for the prophylaxis of anthrax infection in a mammalian subject comprising administering to said subject the vaccine of claim 1.

3. The vaccine of claim 1, wherein the therapeutically effective amount of the live attenuated *B. anthracis* strain is at least $10^7$ spores.

4. The vaccine of claim 1, wherein the therapeutically effective amount of the live attenuated *B. anthracis* strain is at least $10^8$ spores.

* * * * *

SEQUENCE LISTING

<160> NUMBER OF SEQ ID NOS: 27

<210> SEQ ID NO 1
<211> LENGTH: 23
<212> TYPE: DNA
<213> ORGANISM: Artificial
<220> FEATURE:
<223> OTHER INFORMATION: EAI1

<400> SEQUENCE: 1
tgacgtaggc gaaggtacag ttc                                                 23

<210> SEQ ID NO 2
<211> LENGTH: 25
<212> TYPE: DNA
<213> ORGANISM: Artificial
<220> FEATURE:
<223> OTHER INFORMATION: EAI2C

<400> SEQUENCE: 2
aacgttaccc tctgttacgt tcaca                                               25

<210> SEQ ID NO 3
<211> LENGTH: 24
<212> TYPE: DNA
<213> ORGANISM: Artificial
<220> FEATURE:
<223> OTHER INFORMATION: GRO1

<400> SEQUENCE: 3
tcttaactgg tggcgaagta atca                                                24

<210> SEQ ID NO 4
<211> LENGTH: 23
<212> TYPE: DNA
<213> ORGANISM: Artificial
<220> FEATURE:
<223> OTHER INFORMATION: GRO2C

<400> SEQUENCE: 4
ctttaccagc gcgtcctaaa gat                                                 23

<210> SEQ ID NO 5
<211> LENGTH: 24
<212> TYPE: DNA
<213> ORGANISM: Artificial
<220> FEATURE:
<223> OTHER INFORMATION: GRO3

<400> SEQUENCE: 5
gaaggtgacg aagcaacagg tatc                                                24

<210> SEQ ID NO 6
<211> LENGTH: 21
<212> TYPE: DNA
<213> ORGANISM: Artificial
<220> FEATURE:
<223> OTHER INFORMATION: GRO4C

<400> SEQUENCE: 6
ctagaccagc gttgattgcg a                                                   21

<210> SEQ ID NO 7
<211> LENGTH: 38
<212> TYPE: DNA
<213> ORGANISM: Artificial

```
<220> FEATURE:
<223> OTHER INFORMATION: HTRA1

<400> SEQUENCE: 7
ggggaagtaa agcggccgca ttacgacgga ccaaattt                              38

<210> SEQ ID NO 8
<211> LENGTH: 38
<212> TYPE: DNA
<213> ORGANISM: Artificial
<220> FEATURE:
<223> OTHER INFORMATION: HTRA2C

<400> SEQUENCE: 8
cattagcacc atactagtca acaacagcta aatctaac                              38

<210> SEQ ID NO 9
<211> LENGTH: 38
<212> TYPE: DNA
<213> ORGANISM: Artificial
<220> FEATURE:
<223> OTHER INFORMATION: HTRA3

<400> SEQUENCE: 9
gcagattgga atgtcgacgt tattcaaaca gatgcagc                              38

<210> SEQ ID NO 10
<211> LENGTH: 38
<212> TYPE: DNA
<213> ORGANISM: Artificial
<220> FEATURE:
<223> OTHER INFORMATION: HTRA4C

<400> SEQUENCE: 10
cttcttttta ttggcgcgcc tgattctttg tagctgag                              38

<210> SEQ ID NO 11
<211> LENGTH: 54
<212> TYPE: DNA
<213> ORGANISM: Artificial
<220> FEATURE:
<223> OTHER INFORMATION: HTRA5

<400> SEQUENCE: 11
agacctagat cttatacaaa aaggagtacg tatatgggat attacgacgg acca            54

<210> SEQ ID NO 12
<211> LENGTH: 46
<212> TYPE: DNA
<213> ORGANISM: Artificial
<220> FEATURE:
<223> OTHER INFORMATION: HTRA6C

<400> SEQUENCE: 12
agatagacct gaggatcctt attgattctt tgtagctgag ttatct                     46

<210> SEQ ID NO 13
<211> LENGTH: 70
<212> TYPE: DNA
<213> ORGANISM: Artificial
<220> FEATURE:
<223> OTHER INFORMATION: HTRA7

<400> SEQUENCE: 13
cggagaattc taatacgact cactataggt accaccatga ctgtatcatc ttttagttca      60
```

```
gattcaaaag                                                              70

<210> SEQ ID NO 14
<211> LENGTH: 50
<212> TYPE: DNA
<213> ORGANISM: Artificial
<220> FEATURE:
<223> OTHER INFORMATION: HTRA8C

<400> SEQUENCE: 14
gaagatctgc ggccgcccgg gttattgatt ctttgtagct gagttatctg                  50

<210> SEQ ID NO 15
<211> LENGTH: 27
<212> TYPE: DNA
<213> ORGANISM: Artificial
<220> FEATURE:
<223> OTHER INFORMATION: HTRA9

<400> SEQUENCE: 15
caagaaggac acaaaacgtg actatac                                           27

<210> SEQ ID NO 16
<211> LENGTH: 23
<212> TYPE: DNA
<213> ORGANISM: Artificial
<220> FEATURE:
<223> OTHER INFORMATION: HTRA10C

<400> SEQUENCE: 16
gtatagccga taaagaaagt ctc                                               23

<210> SEQ ID NO 17
<211> LENGTH: 24
<212> TYPE: DNA
<213> ORGANISM: Artificial
<220> FEATURE:
<223> OTHER INFORMATION: HTRA11

<400> SEQUENCE: 17
aaattccagt agatatcgat ggcg                                              24

<210> SEQ ID NO 18
<211> LENGTH: 20
<212> TYPE: DNA
<213> ORGANISM: Artificial
<220> FEATURE:
<223> OTHER INFORMATION: HTRA12C

<400> SEQUENCE: 18
taacgcacca ccactgttcc                                                   20

<210> SEQ ID NO 19
<211> LENGTH: 20
<212> TYPE: DNA
<213> ORGANISM: Artificial
<220> FEATURE:
<223> OTHER INFORMATION: HTRB1

<400> SEQUENCE: 19
aaatgatacg ggcgcacttc                                                   20

<210> SEQ ID NO 20
<211> LENGTH: 21
<212> TYPE: DNA
<213> ORGANISM: Artificial
```

```
<220> FEATURE:
<223> OTHER INFORMATION: HTRB2C

<400> SEQUENCE: 20
cacgatcaac agcatccaca a                                            21

<210> SEQ ID NO 21
<211> LENGTH: 22
<212> TYPE: DNA
<213> ORGANISM: Artificial
<220> FEATURE:
<223> OTHER INFORMATION: KANA1

<400> SEQUENCE: 21
gaaggaatgt ctcctgctaa gg                                           22

<210> SEQ ID NO 22
<211> LENGTH: 21
<212> TYPE: DNA
<213> ORGANISM: Artificial
<220> FEATURE:
<223> OTHER INFORMATION: KANA2C

<400> SEQUENCE: 22
ctgatcgacc ggacgcagaa g                                            21

<210> SEQ ID NO 23
<211> LENGTH: 18
<212> TYPE: DNA
<213> ORGANISM: Artificial
<220> FEATURE:
<223> OTHER INFORMATION: NPRA1

<400> SEQUENCE: 23
cgcggagcaa cgattttc                                                18

<210> SEQ ID NO 24
<211> LENGTH: 24
<212> TYPE: DNA
<213> ORGANISM: Artificial
<220> FEATURE:
<223> OTHER INFORMATION: NPRA2C

<400> SEQUENCE: 24
atcatacgct gcattgaaaa catt                                         24

<210> SEQ ID NO 25
<211> LENGTH: 21
<212> TYPE: DNA
<213> ORGANISM: Artificial
<220> FEATURE:
<223> OTHER INFORMATION: SAP1

<400> SEQUENCE: 25
tcgaaatggc tgaccaaaca g                                            21

<210> SEQ ID NO 26
<211> LENGTH: 24
<212> TYPE: DNA
<213> ORGANISM: Artificial
<220> FEATURE:
<223> OTHER INFORMATION: SAP2C

<400> SEQUENCE: 26
accctctggt gaaacaactt cagt                                         24
```

<210> SEQ ID NO 27
<211> LENGTH: 413
<212> TYPE: PRT
<213> ORGANISM: Bacillus anthracis

<400> SEQUENCE: 27

| | | | | | | | | | | | | | | | |
|---|---|---|---|---|---|---|---|---|---|---|---|---|---|---|---|
| Met | Gly | Tyr | Tyr | Asp | Gly | Pro | Asn | Leu | Asn | Glu | Glu | His | Ser | Glu | Thr |
| 1 | | | | 5 | | | | | 10 | | | | | 15 | |
| Arg | Glu | Val | Arg | Lys | Ser | Gly | Ser | Lys | Lys | Gly | Tyr | Phe | Phe | Thr | Gly |
| | | | 20 | | | | | 25 | | | | | 30 | | |
| Leu | Val | Gly | Ala | Val | Val | Gly | Ala | Val | Ser | Ile | Ser | Phe | Ala | Ala | Pro |
| | | | 35 | | | | | 40 | | | | | 45 | | |
| Tyr | Met | Pro | Trp | Ala | Gln | Asn | Asn | Gly | Ala | Thr | Val | Ser | Ser | Phe | Ser |
| | 50 | | | | | 55 | | | | | 60 | | | | |
| Ser | Asp | Ser | Lys | Val | Glu | Gly | Thr | Val | Val | Pro | Val | Val | Asn | Lys | Ala |
| 65 | | | | | 70 | | | | | 75 | | | | | 80 |
| Lys | Asn | Glu | Thr | Asp | Leu | Pro | Gly | Met | Ile | Glu | Gly | Ala | Lys | Asp | Val |
| | | | | 85 | | | | | 90 | | | | | 95 | |
| Val | Val | Gly | Val | Ile | Asn | Met | Gln | Gln | Ser | Ile | Asp | Pro | Phe | Ala | Met |
| | | | | 100 | | | | | 105 | | | | | 110 | |
| Gln | Pro | Thr | Gly | Gln | Glu | Gln | Gln | Ala | Gly | Ser | Gly | Ser | Gly | Val | Ile |
| | | | 115 | | | | | 120 | | | | | 125 | | |
| Tyr | Lys | Lys | Ala | Gly | Asn | Lys | Ala | Tyr | Ile | Val | Thr | Asn | Asn | His | Val |
| | | 130 | | | | | 135 | | | | | 140 | | | |
| Val | Asp | Gly | Ala | Asn | Lys | Leu | Ala | Val | Lys | Leu | Ser | Asp | Gly | Lys | Lys |
| 145 | | | | | 150 | | | | | 155 | | | | | 160 |
| Val | Asp | Ala | Lys | Leu | Val | Gly | Lys | Asp | Pro | Trp | Leu | Asp | Leu | Ala | Val |
| | | | | 165 | | | | | 170 | | | | | 175 | |
| Val | Glu | Ile | Asp | Gly | Ala | Asn | Val | Asn | Lys | Val | Ala | Thr | Leu | Gly | Asp |
| | | | 180 | | | | | 185 | | | | | 190 | | |
| Ser | Ser | Lys | Ile | Arg | Ala | Gly | Glu | Lys | Ala | Ile | Ala | Ile | Gly | Asn | Pro |
| | | 195 | | | | | 200 | | | | | 205 | | | |
| Leu | Gly | Phe | Asp | Gly | Ser | Val | Thr | Glu | Gly | Ile | Ile | Ser | Ser | Lys | Glu |
| | 210 | | | | | 215 | | | | | 220 | | | | |
| Arg | Glu | Ile | Pro | Val | Asp | Ile | Asp | Gly | Asp | Lys | Arg | Ala | Asp | Trp | Asn |
| 225 | | | | | 230 | | | | | 235 | | | | | 240 |
| Ala | Gln | Val | Ile | Gln | Thr | Asp | Ala | Ala | Ile | Asn | Pro | Gly | Asn | Ser | Gly |
| | | | | 245 | | | | | 250 | | | | | 255 | |
| Gly | Ala | Leu | Phe | Asn | Gln | Asn | Gly | Glu | Ile | Ile | Gly | Ile | Asn | Ser | Ser |
| | | | 260 | | | | | 265 | | | | | 270 | | |
| Lys | Ile | Ala | Gln | Gln | Glu | Val | Glu | Gly | Ile | Gly | Phe | Ala | Ile | Pro | Ile |
| | | 275 | | | | | 280 | | | | | 285 | | | |
| Asn | Ile | Ala | Lys | Pro | Val | Ile | Glu | Ser | Leu | Glu | Lys | Asp | Gly | Val | Val |
| | 290 | | | | | 295 | | | | | 300 | | | | |
| Lys | Arg | Pro | Ala | Leu | Gly | Val | Gly | Val | Val | Ser | Leu | Glu | Asp | Val | Gln |
| 305 | | | | | 310 | | | | | 315 | | | | | 320 |
| Ala | Tyr | Ala | Val | Asn | Gln | Leu | Lys | Val | Pro | Lys | Glu | Val | Thr | Asn | Gly |
| | | | | 325 | | | | | 330 | | | | | 335 | |
| Val | Val | Leu | Gly | Lys | Ile | Tyr | Pro | Ile | Ser | Pro | Ala | Glu | Lys | Ala | Gly |
| | | | 340 | | | | | 345 | | | | | 350 | | |
| Leu | Glu | Gln | Tyr | Asp | Ile | Val | Val | Ala | Leu | Asp | Asn | Gln | Lys | Val | Glu |
| | | 355 | | | | | 360 | | | | | 365 | | | |
| Asn | Ser | Leu | Gln | Phe | Arg | Lys | Tyr | Leu | Tyr | Glu | Lys | Lys | Val | Gly |
| | 370 | | | | | 375 | | | | | 380 | | | |

```
Glu Lys Val Glu Val Thr Phe Tyr Arg Asn Gly Gln Lys Met Thr Lys
385                 390                 395                 400

Thr Ala Thr Leu Ala Asp Asn Ser Ala Thr Lys Asn Gln
                405                 410
```